US010244991B2

(12) United States Patent
Shademan et al.

(10) Patent No.: US 10,244,991 B2
(45) Date of Patent: Apr. 2, 2019

(54) METHOD AND SYSTEM FOR PROVIDING RECOMMENDATION FOR OPTIMAL EXECUTION OF SURGICAL PROCEDURES

(71) Applicant: Children's National Medical Center, Washington, DC (US)

(72) Inventors: Azad Shademan, Washington, DC (US); Axel Krieger, Alexandria, VA (US); Jaepyeong Cha, Ellicot City, MD (US); Peter Kim, Washington, DC (US); Jin U. Kang, Glenelg, MD (US)

(73) Assignee: Children's National Medical Center, Washington, DC (US)

( * ) Notice: Subject to any disclaimer, the term of this patent is extended or adjusted under 35 U.S.C. 154(b) by 1069 days.

(21) Appl. No.: 14/625,420

(22) Filed: Feb. 18, 2015

(65) Prior Publication Data
US 2015/0230875 A1 Aug. 20, 2015

Related U.S. Application Data

(60) Provisional application No. 61/940,664, filed on Feb. 17, 2014.

(51) Int. Cl.
  *A62B 5/00* (2006.01)
  *A61B 5/00* (2006.01)
  (Continued)

(52) U.S. Cl.
  CPC .......... *A61B 5/7405* (2013.01); *A61B 5/7425* (2013.01); *A61B 17/0482* (2013.01);
  (Continued)

(58) Field of Classification Search
  CPC ...... A61B 5/7425; A61B 5/441; A61B 5/0261
  See application file for complete search history.

(56) References Cited

U.S. PATENT DOCUMENTS

| 5,556,612 A | 9/1996 | Anderson et al. |
| 2009/0148402 A1 | 6/2009 | Brunetta et al. |

(Continued)

FOREIGN PATENT DOCUMENTS

| WO | WO 2010/066827 A1 | 6/2010 |
| WO | WO 2010/120769 A2 | 10/2010 |
| WO | WO 2010/120769 A3 | 10/2010 |

OTHER PUBLICATIONS

International Search Report and Written Opinion of the International Searching Authority dated May 19, 2015 in PCT/US2015/012669.

(Continued)

*Primary Examiner* — Rajeev Siripurapu
(74) *Attorney, Agent, or Firm* — Oblon, McClelland, Maier & Neustadt, L.L.P.

(57) ABSTRACT

The present disclosure is related to a method and apparatus for providing recommendation for a medical surgical procedure, including acquiring, using circuitry, a plurality of multispectral images representing a portion of an anatomy of a patient, performing image processing on each of the plurality of multispectral images to form a plurality of value maps, each value map identifying aspects of the portion of the anatomy by assigned values, combining the plurality of value maps into a single recommendation map, determining optimal points for performing the medical surgical procedure based on the single recommendation map, and displaying the optimal points for the medical surgical procedure by overlaying the optimal points on an original image of the portion of the anatomy or applying the optimal points to a robotic medical surgical procedure.

21 Claims, 13 Drawing Sheets

(51) Int. Cl.
  *A61B 17/32* (2006.01)
  *G06T 7/00* (2017.01)
  *A61B 17/04* (2006.01)
  *G06T 7/12* (2017.01)
  *G06T 7/62* (2017.01)
  *G06T 7/194* (2017.01)
  *G06F 19/00* (2018.01)
  *A61B 5/026* (2006.01)
  *A61B 17/068* (2006.01)
  *A61B 17/00* (2006.01)
  *A61B 34/30* (2016.01)
  *A61B 34/10* (2016.01)

(52) U.S. Cl.
  CPC ............ *A61B 17/32* (2013.01); *G06F 19/00* (2013.01); *G06T 7/0012* (2013.01); *G06T 7/12* (2017.01); *G06T 7/194* (2017.01); *G06T 7/62* (2017.01); *A61B 5/0261* (2013.01); *A61B 5/489* (2013.01); *A61B 5/4836* (2013.01); *A61B 17/068* (2013.01); *A61B 34/30* (2016.02); *A61B 2017/00061* (2013.01); *A61B 2034/105* (2016.02); *A61B 2034/107* (2016.02); *A61B 2560/0475* (2013.01); *A61B 2560/0487* (2013.01); *A61B 2576/02* (2013.01); *G06T 2207/10024* (2013.01); *G06T 2207/10048* (2013.01); *G06T 2207/20064* (2013.01); *G06T 2207/20081* (2013.01); *G06T 2207/20104* (2013.01); *G06T 2207/30096* (2013.01); *G06T 2207/30101* (2013.01); *G06T 2207/30172* (2013.01)

(56) References Cited

U.S. PATENT DOCUMENTS

| | | |
|---|---|---|
| 2010/0113474 A1 | 5/2010 | Zacharhuk et al. |
| 2011/0111018 A1 | 5/2011 | Ashraf et al. |
| 2011/0295062 A1 | 12/2011 | Gratacós Solsona et al. |
| 2012/0029348 A1 | 2/2012 | Yaroslavsky et al. |
| 2013/0131429 A1 | 5/2013 | Toone et al. |

OTHER PUBLICATIONS

Extended European Search Report dated Aug. 11, 2017 in Patent Application No. 15749662.1.
Randal S. Baker, et al. "The Science of Stapling and Leaks," Obesity Surgery, vol. 14, XP055395303, 2004, pp. 1290-1298.
Guolan Lu, et al. "Medical Hyperspectral imaging: a review," Journal of Biomedical Optics, vol. 19, XP055394861, 2014, 24 Pages.
Cemil Kirbas, et al. "A Review of Vessel Extraction Techniques and Algorithms," ACM Computing Surveys, vol. 36, No. 2, XP058286852, 2004, pp. 81-121.

METHOD AND SYSTEM FOR PROVIDING RECOMMENDATION FOR OPTIMAL EXECUTION OF SURGICAL PROCEDURES

CROSS-REFERENCE TO RELATED APPLICATIONS

This application is based upon and claims the benefit of priority under 35 U.S.C. § 119(e) from U.S. Ser. No. 61/940,664, filed Feb. 17, 2014, the entire contents of which are incorporated herein by reference.

FIELD OF THE INVENTION

This disclosure is related to the field of intelligent medical devices, namely, a system and method for smart and optimal execution of surgical procedures on all types of tissues including soft and bony tissues using multimodal information including optical images and/or anatomical information. Specifically, the present disclosure is related to a method and system for providing recommendation to a surgeon or a surgical system regarding portions of a patient's anatomy that are appropriate for surgical procedure and portions of the patient's anatomy that are not appropriate for surgical procedure.

BACKGROUND

Several surgical procedures and interventions require precise tissue manipulation or insertion of surgical instruments and/or accessories in the body. To carry out the optimal procedural and technical tasks, several factors must be taken into consideration to place surgical instruments and/or accessories in soft tissue or bone, or perform procedures like incision, cuts, removals, suturing, stitching, etc. These factors include, but are not limited to, minimizing complication risk, reducing pain, and accelerating recovery time. To assist a surgeon or a surgical system (for example, a robot) in making a better decision on where to interact with tissue, advanced imaging systems and analysis software which provide decision support for optimal outcome must be developed.

Multispectral image acquisition is an advanced imaging technique to capture scene information at different spectral wavelengths. Multispectral images provide structural properties of scene objects that may not be visible from a single channel (i.e., a single channel corresponding to an image obtained using a particular spectral wavelength). Multispectral images can also reveal subsurface structures at higher wavelengths (near-infrared and infrared wavelengths). In medicine, multispectral imaging has been widely used in cancer detection and blood oxygen saturation observations from skin. Polarization-sensitive imaging is another advanced imaging technique that utilizes the scattering and polarization properties of light propagating in the tissue. By adjusting polarization states depending on the light penetration depth, polarization control techniques can be used for depth-selective measurement. An advantage of polarization-sensitive imaging is the elimination of specular reflection from the tissue surface and clear identification of deep tissue structures, which is useful for the surgical procedures and interventions.

U.S. Pat. No. 8,285,015 describes an image acquisition device which forms multispectral images from decomposition of an image into multiple component parts based on the type of imaging, but does not disclose any quantitate post-processing of acquired images. While there has been work in developing multispectral and polarization-sensitive imaging systems, there are currently no systems that analyze and quantify the images from multispectral and polarization-sensitive imaging systems to provide recommendations regarding portions of a patient's anatomy that are appropriate for surgical procedure and other portions of the patient's anatomy that are not appropriate for surgical procedure.

Blood vessels should be avoided during suturing to mitigate tissue damage and encourage faster recovery. U.S. Pat. No. 8,611,629 describes an interactive method for blood vessel analysis. A user indicates a position on a vessel of the tubular structure, which is then used to identify a portion of the tubular structure situated around the indicated position, including any bifurcations, and extending up to a predetermined distance measured from the indicated position, for obtaining an identified portion. Other blood vessel segmentation algorithms have been described in the literature. Bankhead et al., included along with the information disclosure statement, describes a fast and accurate unsupervised algorithm to detect blood vessels based on undecimated wavelet transform. Blood vessel segmentation provides limited structural information of a patient's anatomy and therefore, has not been used for providing recommendations to a surgeon or a surgical system regarding portions of the patient's anatomy that are appropriate for surgical procedure and portions of the patient's anatomy that are not appropriate for surgical procedure.

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

SUMMARY

An exemplary embodiment of the present disclosure describes a method and apparatus for providing recommendation for a medical surgical procedure. For example, an exemplary embodiment of the present disclosure describes optimal execution of surgical procedures and optimal placement of surgical instruments and accessories, including but not limited to, implants, and prostheses in the tissue from multi-modality imaging and anatomical cues for manual, semi-automated, and automated surgery.

The surgical instruments and tools, implants and prostheses include, but are not limited to, sutures, needles, clips, staples, screws, valves and guidance markers. They need to be placed in the tissue optimally to reduce complications and accelerate recovery time.

The procedures and interventions include, but are not limited to, surgical cuts, incisions, suturing, stitching and other tissue manipulation procedures sensitive to vulnerable tissue.

The multiple cues come from different imaging modalities, including but not limited to, multispectral images, MRI, CT, as well as quantification of anatomical descriptions and geometrical shapes.

In an exemplary embodiment of the present invention, a multispectral imaging system is provided that is capable of generating and displaying a map of blood vessels and tissue density and subsurface tissue information and outlining recommendation for non-vulnerable tissue regions for surgical procedures and interventions that should avoid blood vessels.

In an exemplary embodiment of the present invention, a multispectral system and method are designed to automatically generate optimal suture placement locations for bowel anastomosis by avoiding vulnerable tissue regions including thin tissue, mesentery, and blood vessels.

In another exemplary embodiment, the disclosure allows in its decision support of real-time precise and accurate target tissue information of mobile deformable tissue.

BRIEF DESCRIPTION OF THE DRAWINGS

A more complete appreciation of the disclosed embodiments and many of the attendant advantages thereof will be readily obtained as the same becomes better understood by reference to the following detailed description when considered in connection with the accompanying drawings, wherein.

DETAILED DESCRIPTION

Figure 1:
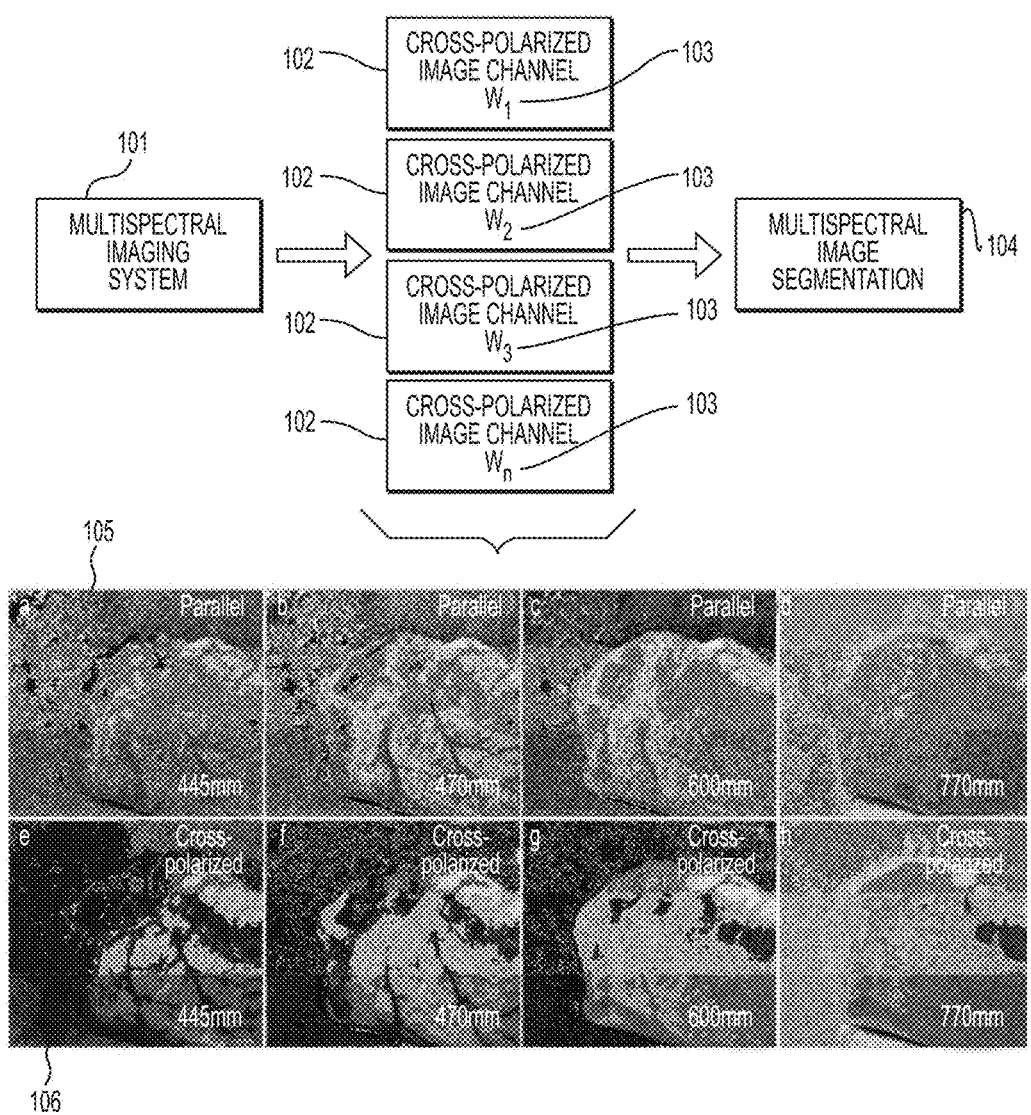
FIG. 1 illustrates generation and segmentation of multispectral images.

The present invention is related to a method for providing information for a medical surgical procedure, the method comprising acquiring, using circuitry, a plurality of multispectral images representing a portion of a patient's anatomy, performing image processing on each of the plurality of multispectral images to form a plurality of value maps, each value map identifying aspects of the portion of the patient's anatomy by assigned values, combining the plurality of value maps into a single recommendation map, determining optimal points for performing the medical surgical procedure based on the single recommendation map, and displaying the optimal points for the medical surgical procedure by overlaying the optimal points on an original image of the portion of the patient's anatomy or applying the optimal points to a robotic medical surgical procedure.

The method further comprises calculating diffuse reflectance values for the plurality of multispectral images, selecting a reference diffuse reflectance value from the diffuse reflectance values and determining corresponding ratios between corresponding diffuse reflectance values and the reference diffuse reflectance value, and determining a thickness map, as one of the plurality of value maps, corresponding to thickness of different portions of the patient's anatomy based on the determined corresponding ratios.

The method further comprises extracting a foreground and a background from the plurality of multispectral images to extract blood vessels, and determining a vessel map, as one of the plurality of value maps, corresponding to vessels in different portions of the patient's anatomy based on said extracting.

The method further comprises analyzing proportions of corresponding signal intensity of the plurality of multispectral images, and determining a perfusion map, as one of the plurality of value maps, corresponding to an amount of blood perfusion in different portions of the patient's anatomy based on said analyzing.

The present invention is related to a method for providing information for a medical surgical procedure, wherein said extracting said foreground includes applying a blood vessel segmentation algorithm to the plurality of multispectral images, and extracting a centerline or a vessel skeleton from the plurality of multispectral images based on said blood vessel segmentation algorithm.

The present invention is related to a method for providing information for a medical surgical procedure, wherein the optimal points for the medical surgical procedure are determined based on calculation of local maxima in the single recommendation map, which includes the thickness map, wherein the optimal points for the medical surgical procedure are determined based on calculation of local maxima in the single recommendation map, which includes the vessel map, and wherein the plurality of multispectral images are cross-polarized image, wherein the plurality of multispectral images are parallel polarization images.

The present invention is related to a method for providing information for a medical surgical procedure, wherein the plurality of value maps include dark portions of the patient's anatomy and bright portions of the patient's anatomy, and wherein the dark portions of the patient's anatomy indicate portions of the patient's anatomy that need to be avoided during the medical surgical procedure and the bright portions of the patient's anatomy indicate other portions of the patient's anatomy that are appropriate for the medical surgical procedure, and wherein the plurality of value maps include a scale indicating values from 0 to 1, wherein the values closer to 0 correspond to the dark portions of the patient's anatomy and the values closer to 1 correspond to the bright portions of the patient's anatomy.

The present invention is related to a method for providing information for a medical surgical procedure, wherein each of the plurality of value maps corresponds to a different portion of the patient's anatomy, and wherein each of the plurality of value maps corresponds to a different anatomical feature of the patient's anatomy.

The method further comprises segmenting the representation of the portion of a patient's anatomy to form a plurality of segmented images based on predetermined anatomical or geometric information, wherein the medical surgical procedure is at least one of suturing and stapling and the optimal points is at least one of optimal suture and stapling points, and wherein the medical surgical procedure is cutting.

The present invention is also related to an apparatus for providing information for a medical surgical procedure comprising circuitry configured to acquire a plurality of multispectral images representing a portion of a patient's anatomy, perform image processing on each of the plurality of segmented images to form a plurality of value maps, each value map identifying aspects of the portion of the patient's anatomy by assigned values, combine the plurality of value maps into a single recommendation map, determine optimal points for performing the medical surgical procedure based on the single recommendation map, and display the optimal points for the medical surgical procedure by overlaying the optimal points on an original image of the portion of the patient's anatomy or apply the optimal points to a robotic medical surgical procedure.

The apparatus further comprises circuitry configured to calculate diffuse reflectance values for the plurality of multispectral images, select a reference diffuse reflectance value from the diffuse reflectance values and determine corresponding ratios between corresponding diffuse reflectance values and the reference diffuse reflectance value, and determine a thickness map, as one of the plurality of value maps, corresponding to thickness of different portions of the patient's anatomy based on the determined corresponding ratio.

The apparatus further comprises circuitry configured to extract a foreground and a background from the plurality of multispectral images to extract blood vessels, and determine a vessel map, as one of the plurality of value maps, corresponding to vessels in different portions of the patient's anatomy based on the extracted foreground and background.

The apparatus further comprises circuitry configured to analyze proportions of corresponding signal intensity of the plurality of multispectral images; and determine a perfusion map, as one of the plurality of value maps, corresponding to an amount of blood perfusion in different portions of the patient's anatomy based on said analyzed proportions.

The apparatus further comprises circuitry configured to apply a blood vessel segmentation algorithm to the plurality of multispectral images, and extract a centerline or a vessel skeleton from the plurality of multispectral images based on said blood vessel segmentation algorithm in order to extract the foreground.

The present invention is related to an apparatus for providing information for a medical surgical procedure, wherein the optimal points for the medical surgical procedure are determined based on calculation of local maxima in the single recommendation map, which includes the thickness map, wherein the optimal points for the medical surgical procedure are determined based on calculation of local maxima in the single recommendation map, which includes the vessel map, and wherein the plurality of multispectral images are at least one of cross-polarized images and parallel polarization images.

The present invention is related to an apparatus for providing information for a medical surgical procedure, wherein the plurality of value maps include dark portions of the patient's anatomy and bright portions of the patient's anatomy, and wherein the dark portions of the patient's anatomy indicate portions of the patient's anatomy that need to be avoided during the medical surgical procedure and the bright portions of the patient's anatomy indicate other portions of the patient's anatomy that are appropriate for the medical surgical procedure, and wherein the plurality of value maps include a scale indicating values from 0 to 1, wherein the values closer to 0 correspond to the dark portions of the patient's anatomy and the values closer to 1 correspond to the bright portions of the patient's anatomy.

The present invention is also related to a non-transitory computer-readable storage medium including computer-readable instructions, that when executed by a computer, cause the computer to execute a method for providing information for a medical surgical procedure, the method comprising acquiring a plurality of multispectral images representing a portion of a patient's anatomy, performing image processing on each of the plurality of multispectral images to form a plurality of value maps, each value map identifying aspects of the portion of the patient's anatomy by assigned values, combining the plurality of value maps into a single recommendation map, determining optimal points for performing the medical surgical procedure based on the single recommendation map, and displaying the optimal points for the medical surgical procedure by overlaying the optimal points on an original image of the portion of the patient's anatomy or applying the optimal points to a robotic medical surgical procedure.

In many surgical procedures and interventions, a soft tissue region needs to be removed and the remaining regions must be reconnected again. Recovery from this kind of procedure depends on maximal blood flow and proper blood oxygenation in the uncut tissue. The current practice is to avoid major blood vessels as visible to the naked eye or through visible-range cameras, but many other factors are neglected. For example, there are no systems to quantify tissue vulnerability and rank them based on thickness. There are also no guidelines and commercial devices to minimize the number of cut micro-vessels to accelerate recovery. Surgeons use their experience and years of training to make decisions. Sometimes, they even manually manipulate a tissue to evaluate if it is strong and stable enough to be cut and/or reconnected. The present disclosure describes a system and method that provides relevant quantitative information to assist surgeons or surgical systems in making better decisions on where to manipulate the tissue (e.g., cut and reconnect the tissue). The system and method described here could be applied to either soft tissue procedures such as bowel anastomosis or hard tissue procedures such as bone replacements.

An example of a soft tissue operation is intestinal anastomosis, a common surgical procedure to reconnect the bowel after removal of a pathological condition that affects it. Intestinal anastomosis can be performed in either open surgery or minimally invasive surgery (MIS) settings. Most open surgeries are performed by a surgeon's visual perception and recognition without an intermediary imaging system. Human visual ability has limitations in distinguishing subsurface anatomical structures of a patient's anatomy. It is clear that proper imaging systems that enable visualization of subsurface structures of a patient's anatomy would enhance surgeons' perception and assist them in performing surgery. In MIS, the surgeon perceives what is available through an endoscopic imaging system or via other noninvasive imaging systems. MIS procedures could benefit from multi-modality imaging systems that provide quantitative sensory information in addition to what the surgeon can see. This includes visualizing what is beneath the surface of a tissue and avoiding vulnerable tissue regions.

However, current commercial endoscope systems have limitations in spectral analysis and polarization-sensitive imaging, since there are the birefringence materials at the entrance and exit windows with no spectral filters which make it difficult to apply multispectral and polarization imaging. Birefringence is the optical property of a material having a refractive index that depends on the polarization and propagation direction of light. While there have been remarkable advances in the surgical imaging systems that are geared towards improving surgical vision and the outcome of surgical procedures, there is a clear gap for systems that are capable of quantitative analysis and generating recommendations for better surgical outcomes. This disclosure addresses system and methods that can assist a surgeon or a surgical system to achieve better surgical outcomes by providing quantitative analysis of the surgical scene from multiple input sources and media.

In one embodiment, an imaging system that recommends anastomosis placements to surgeons is described. The system of the present disclosure implements a multispectral imaging system and image analysis methods. Vulnerable tissue regions including blood vessels are identified and segmented. Optimal coordinate points for suture placements are recommended to the surgeon. This is visualized by generating suturing maps, which maps the optical field-of-view to a 2D (or 3D) map of values in the [0, 1] range, where 0 refers to the most vulnerable tissue or other regions that must be avoided by the surgeon and 1 refers to the most desirable and least vulnerable tissue region. A suturing map is obtained by fusing different maps, obtained from several different cues. These cues come from image processing of multispectral images and/or numerical encoding of anatomical information and geometrical structures. Anatomical descriptions may be derived from an anatomy atlas or from a surgeon's description.

An example of cues obtained from multispectral image processing is segmentation of tissue and non-tissue background by comparing pixel values in different wavelengths. Another example of cues obtained from multispectral image processing is the calculation of boundaries for different tissue sections based on tissue thickness. This is possible because absorption and scattering of light is a function of wavelength and surface material. In case of internal organs, different tissue types reflect light differently, which can be encoded into numbers by processing multispectral images. Higher wavelengths penetrate deeper into tissue and as a result, images captured at a higher spectral band reveal the subsurface structures of a patient's anatomy which can be segmented using routine image processing methods. In addition, tissue thickness can be parameterized based on the pixel intensity values measured at higher wavelength bands.

Similar to enumeration of cues from multispectral images, information on geometrical shapes and structures of a patient's anatomy can also be enumerated and used as geometrical cues and mapped to false-color images for integration to the output from multispectral image processing algorithms. Geometric and structural information is derived from either clinical experts, who describe a typical location of anatomical, geometric, or structural landmarks, or from medical Atlases, which tabulate typical anatomical, geometric location, size, and other structural and/or geometric information of organs and other bodily structures relative to other structures. For example, to enumerate the geometric information corresponding to a map for approximate location of suture placements to be approximately 2 mm away from the lumen cut line, a smooth bell-shaped surface could be used to enumerate this information, where the peak of the bell-shaped surface is 2 mm away from the cut line, gradually attenuating from the peak to zero as it gets farther from the peak. The slope and peak location of the bell-shaped curve are functions of the lumen size. The geometrical information will be used in conjunction with the tissue information obtained from information obtained from multispectral image processing.

In an exemplary embodiment, the lumen cut line is first calculated by multispectral image segmentation and boundary segmentation from foreground/background image processing algorithm applied to multispectral images. The length of the cut line is related to the lumen size, which can be calculated from counting the pixels of the segmented cut line. The peak location of the bell-shaped curve is a function of the lumen size and thickness. In an exemplary embodiment, approximately 2 mm was used as one example. The actual value, however, is calculated within the multispectral image processing algorithm. The peak identifies a strong candidate for suture placement, but off-peak values are not dismissed. Rather, the off-peak values are given less weight which in conjunction to other cues could be better candidates for suture placement.

In one embodiment, as illustrated in FIG. 1, image segmentation of cross-polarized images 106 received from a multispectral imaging system 101 is illustrated. The multispectral imaging system 101 includes remote sensing radiometers and other circuitry for acquiring multispectral images of a portion of a patient's anatomy. Additionally, the multispectral imaging system 101 also includes circuitry for acquiring cross-polarized images and parallel-polarized images at various spectral bands/wavelengths 103. Cross-polarization or parallel polarization of the multispectral images enhances the multispectral images, for example, by removing glare. Cross-polarized image channels 102 are obtained from several spectral bands 103 at $w_1, w_2, \ldots, w_n$ light wavelengths. The cross-polarized channels include cross-polarized images 106 imaged at different light wavelengths (i.e., $w_1, w_2, \ldots, w_n$).

Although FIG. 1 illustrates cross-polarized image channels 102, it should be understood that parallel polarization image channels may also be implemented with the multispectral imaging system 101. Parallel polarization image channels would include parallel polarization images 105, as illustrated in FIG. 1. Parallel polarization images 105 and cross-polarized images 106 depicted in FIG. 1 illustrate a cut section of a porcine intestine imaged at four different visible and near-infrared wavelengths (i.e., 445 nm, 470 nm, 600 nm, 770 nm).

After the cross-polarized images 106 are imaged at four different visible and near-infrared wavelengths, they are input into a multispectral image segmentation system 104. The multispectral image segmentation system 104 includes circuitry that performs segmentation of the cross-polarized images 106. Segmentation of the cross-polarized images 106 can be performed using various methods. Examples of segmentation of cross-polarized images 106 include, but are not limited to, blood vessel segmentation, segmentation based on thickness of tissue, segmentation of different tissue types (e.g., fat, muscle), and segmentation of different layers/portions of a patient's anatomy (e.g., inner layer, outer layer, upper portion, lower portion).

Figure 2:
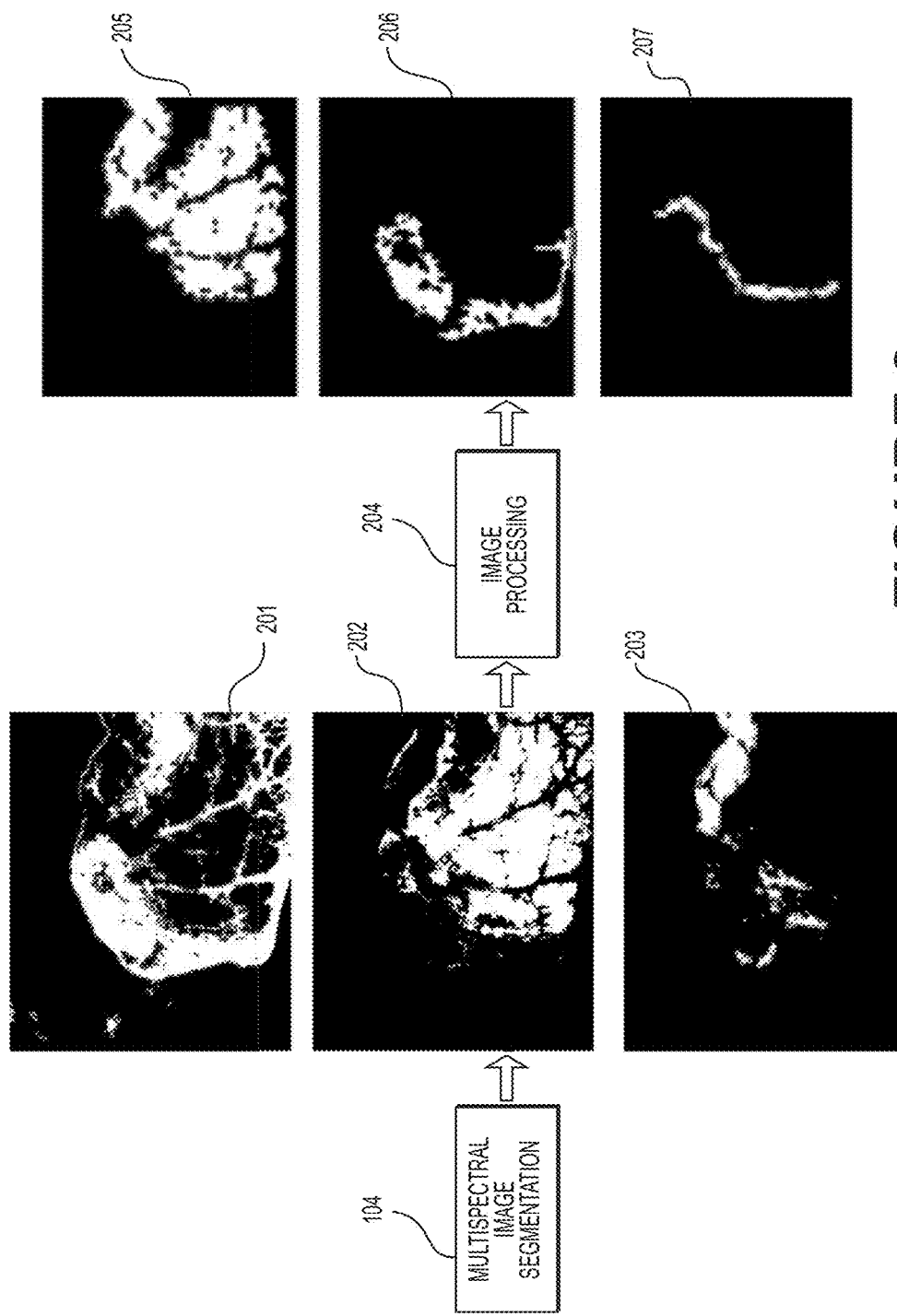
FIG. 2 illustrates segmentation and image processing of multispectral images.

The cross-polarized image channels 102, which include corresponding cross-polarized images 106, are the input signals to the multispectral segmentation system 104 for segmenting the cross-polarized images 106 and generating maps, as illustrated in FIG. 2. Various different methods can be used to segment the cross-polarized images 106 (see above for examples of segmentation) and to generate maps (which will be discussed in more detail below with regard to FIGS. 2 and 6-9). The segmentation of the cross-polarized images 106 results in one or more segmented images 201-203 (see FIG. 2) corresponding to background, foreground, different tissue types, and different anatomical structures.

FIG. 2 illustrates a result of multispectral segmentation, by the multispectral image segmentation system 104, of the cross-polarized images 106 that results in various segmented images 201, 202, and 203, where each segmented image corresponds to different tissues and/or anatomical structures. These segmented images 201, 202, and 203 of a patient's anatomy are produced based on a single cross-polarized image 106 or multiple cross-polarized images 106. Although only three segmented images 201, 202, and 203 are illustrated in FIG. 2, it should be noted that many more segmented images can be produced based on different segmentation methods (i.e., segmentation based on different tissue types, segmentation based on blood vessels, segmentation based on tissue thickness, and perfusion differentiation).

The goal of the multispectral image segmentation algorithm is to process two or more images of the same scene captured at different wavelengths and output information about the contextual information about the scene. For example, visible-light images of outdoor foggy scenes do not provide as much information about the scene as combination of two images captured at Short Wave Infrared and Long Wave Infrared spectral bands. In a surgical site, tissue and medical devices are often covered by blood. Therefore, normal visible-light images do not provide adequate information about the tissue. In addition, certain high bandwidth spectral bands are capable of visualizing shallow subsurface structures.

Multispectral image segmentation can be performed using either supervised or unsupervised methods. In supervised segmentation, a small region of interest (ROI) is specified by a user as labeled training data for a desired tissue to be segmented. This ROI is a numerical array of numbers for each spectral band in the input. Each multispectral pixel, therefore, contains a vector of intensity values with the size of the vector equal to the number of spectral bands. A supervised segmentation algorithm analyzes the training data to produce inferred mapping for new examples. The segmentation algorithm uses Principle Component Analysis (PCA) or a derivative algorithm to find the principle components (PCs) of all the vectors in each ROI. Other vectors outside the ROI which are close to the PCs are labeled as the same segment. This method can be repeated for several tissue types as supervised by the user. Each segmented region can be represented as a binary mask (for example, segmented image 201), where 1 denotes belonging to the region of interest, and 0 denoting otherwise.

In unsupervised segmentation, an unsupervised learning algorithm is used to find the feature vectors that represent each segment in the multispectral image data. The output is similar to supervised learning, but the training data does not need to be labeled. Although different segmentation methods are described above, the present disclosure is directed to using information obtained from multispectral segmentation algorithms to provide recommendation for optimal execution of surgical procedures.

The three segmented images 201, 202, and 203 correspond to either a single cross-polarized image 106 or multiple cross-polarized images 106 and such segmented images 201, 202, and 203 can also be created for single/multiple parallel polarization images 105. For example, segmented image 201 illustrates the inside layers of a porcine intestine, namely the mucosa, the mesentery, and some blood veins and arteries. Segmented image 202, for example, illustrates mainly the outer layer of the porcine intestine, namely the serosa and segmented image 203, for example, illustrates the mesenteric layer and other vulnerable features around a cut line. The cut line, for example, refers to a previous cut made to the patient's anatomy that needs to be sutured. Specifically, the cut line refers to a border line between two different tissue types, e.g. inner and outer layer, or outer layer and background. For instance, the cut line can be determined by intersecting the inner layer segmented image 201 and the outer layer segmented image 202.

Further, image processing 204 is performed on the segmented images 201, 202, and 203 to produce value maps 205, 206, and 207. Image processing 204 may be performed using a processor and/or circuitry. Value map 205 corresponds to an inside layer of the patient's anatomy and value map 206 corresponds to an outside layer of the patient's anatomy. Value map 207 is a map corresponding to the cut line mentioned above and can be determined based on an intersection of the value map 205 and the value map 206. Value maps may correspond to a tissue thickness map, vessel map, and/or perfusion map. A perfusion map can be determined, as a value map, corresponding to an amount of blood perfusion in different portions of a patient's anatomy by analyzing proportions of signal intensity of a plurality of multispectral images. Although FIG. 2 illustrates that segmented images 201, 202, and 203 are processed to generate value maps 205, 206, and 207, it should be noted that value maps 205, 206, and 207 can be generated without segmentation of the multispectral images. In other words, the multispectral images can be directly processed to generate value maps 205, 206, and 207.

Each of the pixels in each of the value maps 205, 206, and 207 are assigned a value between 0 and 1 for each tissue parameter that has been calculated. For example, thick tissue that can be sutured well is assigned a value of 1 and paper thin tissue is assigned a value of 0 and values between 0 and 1 are assigned to tissue based on the tissue's thickness. Although the value maps 205, 206, and 207 illustrated in FIG. 2 correspond to different tissue layers of a patient's anatomy, the value maps can also be created for determining blood vessels within the patient's anatomy. For example, blood vessels that should be avoided are assigned a value of 0 and if no blood vessels are present, that portion of the patient's anatomy is assigned a value of 1. Small vessels that may cause little bleeding during a surgical procedure can be assigned values between 0 and 1.

Further image processing can be performed where a processor and/or circuitry multiplies different values maps 205, 206, and 207 to generate a combined map (see Steps 1107 and 1109 in FIG. 11) with final values for each pixel to determine how good a particular pixel is for suturing (or any other surgical procedure). Further, during image processing 204, different gains (constants that get multiplied with pixel values) can be assigned to each parameter value to emphasize or deemphasize a tissue parameter.

The generation of value maps 205, 206, and 207 allows a surgeon or a surgical system to identify portions of a patient's anatomy that are suitable for surgical procedure and other portions that are not appropriate for surgical procedure. As illustrated above, FIG. 2 provides an example of an anatomical feature of a patient that can be automatically processed from raw input images. Thus, FIG. 2 illustrates the generation of segmented images 201, 202, and 203 using various multispectral segmentation methods discussed above and the generation of values maps 205, 206, and 207 corresponding to a patient's anatomy to allow a surgeon or a surgical system to identify portions of the patient's anatomy that are suitable for surgical procedure and other portions that are not appropriate for surgical procedure.

Figure 3:
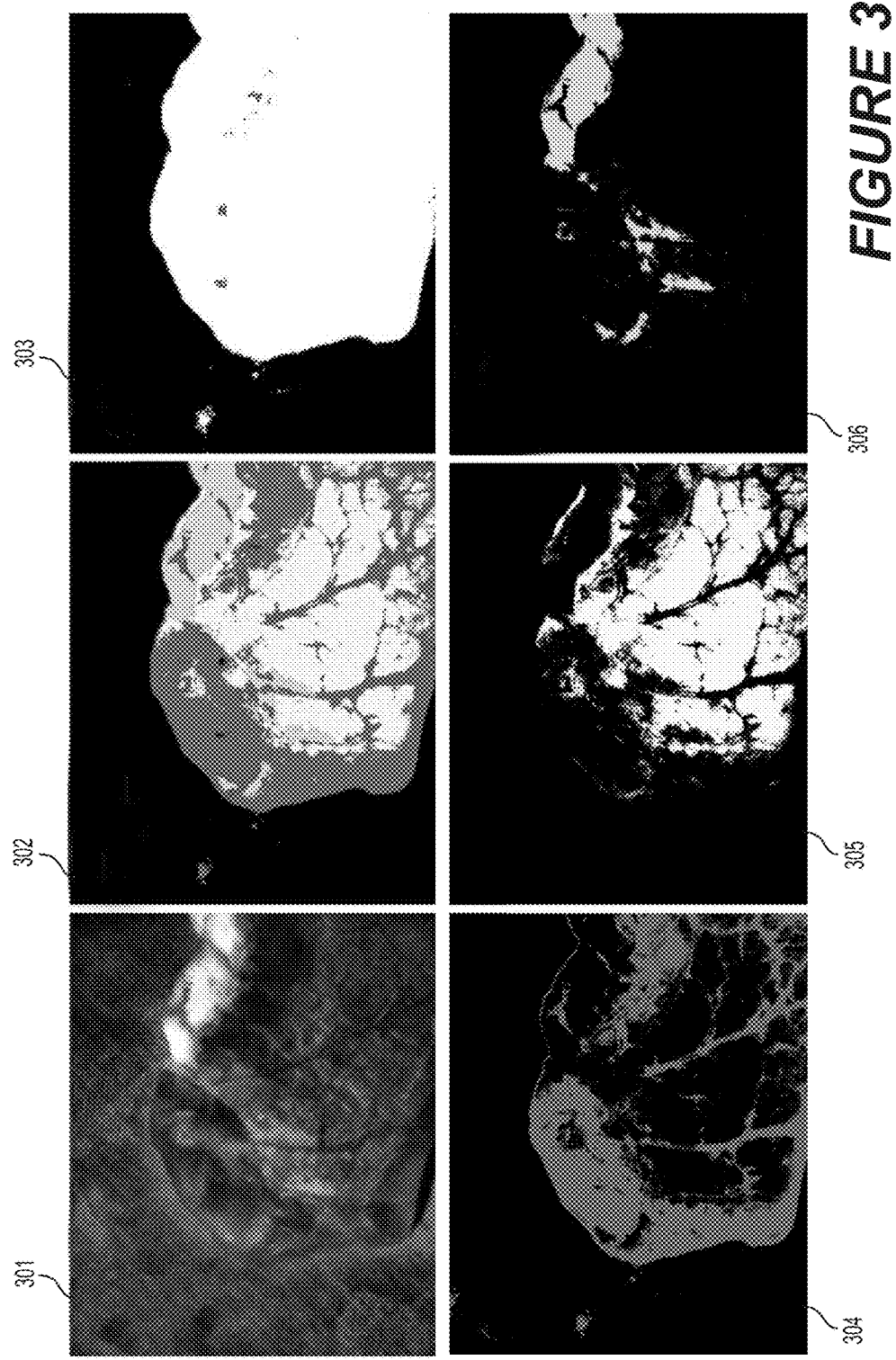
FIG. 3 illustrates results of supervised multispectral image segmentation.

FIG. 3 illustrates supervised multispectral image segmentation to segment tissue regions as specified by a user in offline training. Multispectral images (i.e., cross-polarized images 106 and/or parallel polarization images) are used as input and shown in a false-color in image 301. The multispectral images can be segmented into different regions, as illustrated in image 302. Also, the multispectral images can be segmented such that patient's anatomy (for example, porcine intestine) can be distinguished from the background (i.e., foreground-background segmentation, as illustrated in image 303). Further, the multispectral images can be segmented such that the vulnerable region is illustrated in image 304, the stable tissue region is illustrated in image 305, and the mesenteric tissue is illustrated in image 306. Although the above describes manual segmentation, segmentation of the multispectral images to form images 302, 303, 304, 305, and 306 may be performed using a particularly programmed processor and/or circuitry.

Figure 4:
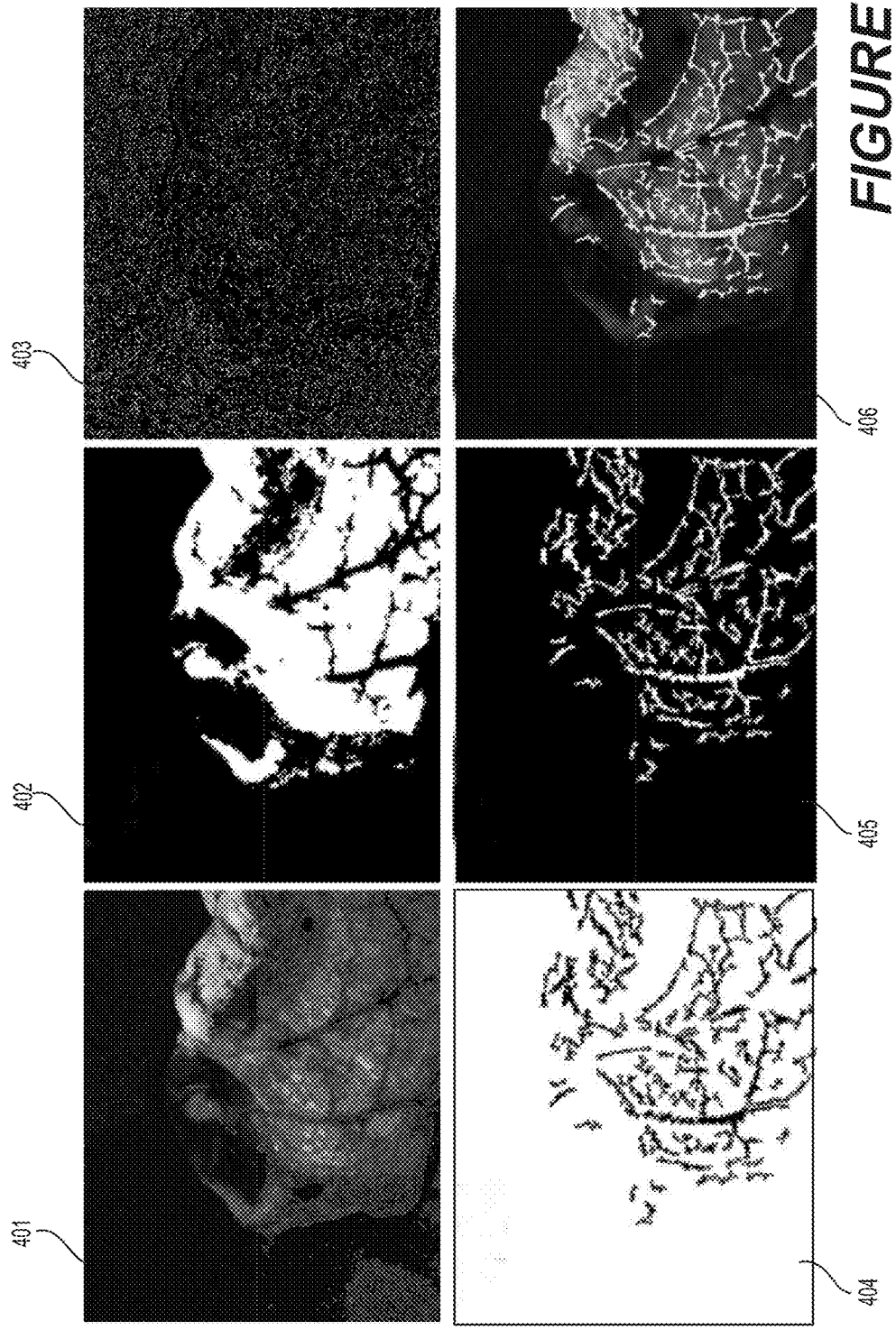
FIG. 4 illustrates blood vessel segmentation.

FIG. 4 illustrates extraction of blood vessels from post-processing of a single channel image 401. The single channel image 401 corresponds to one of parallel polarization images 105 and cross-polarized images 106 generated by the multispectral imaging system 101. For example, a 470 nm cross-polarized image 401 shows high blood vessel contrast compared to other wavelength bands. The single channel image 401 is first pre-processed in order to extract the foreground from the background (see image 402). The processing of the foreground to extract blood vessels contains two main steps. The first step applies a blood vessel segmentation algorithm, e.g., the Isotropic Undecimated Wavelet Transform (IUWT) which extracts vessel segmentation by processing the wavelet coefficients, as illustrated in image 403. The second step includes extraction of the centerlines or the vessel skeleton. This can be achieved by a graph-based algorithm which extracts centerlines by utilizing spline fitting to find out the vessel orientations and the zero-crossings of the second derivative perpendicular to the blood vessels and localization of the blood vessel edges from image profiles 404 and 405. In image 404, vessels are segmented by removing connected objects and filling holes.

To remove noise and scattered pixels from the centerline computation, a standard morphological thinning algorithm is utilized. This results in a value map (for example, a binary map illustrated in image 405) of blood vessels which can be overlaid on the original image for visualization, as illustrated in image 406. The binary map (for example, image 405) is convolved to a smooth bell-curved function to obtain a blood vessel avoidance map, as illustrated in image 406, where a value of 1 denotes no blood vessels and value of 0 denotes blood vessels. Values closer to 1 refer to a less vulnerable region, whereas values closer to 0 refer to proximity to blood vessels. This vessel avoidance map illustrated in image 406 is further fused with other maps using a fusion operator, which will be described in more detail with regard to FIGS. 10 and 11. The processing of images 401-406 may be performed using a particularly programmed processor and/or circuitry.

Figure 5A:
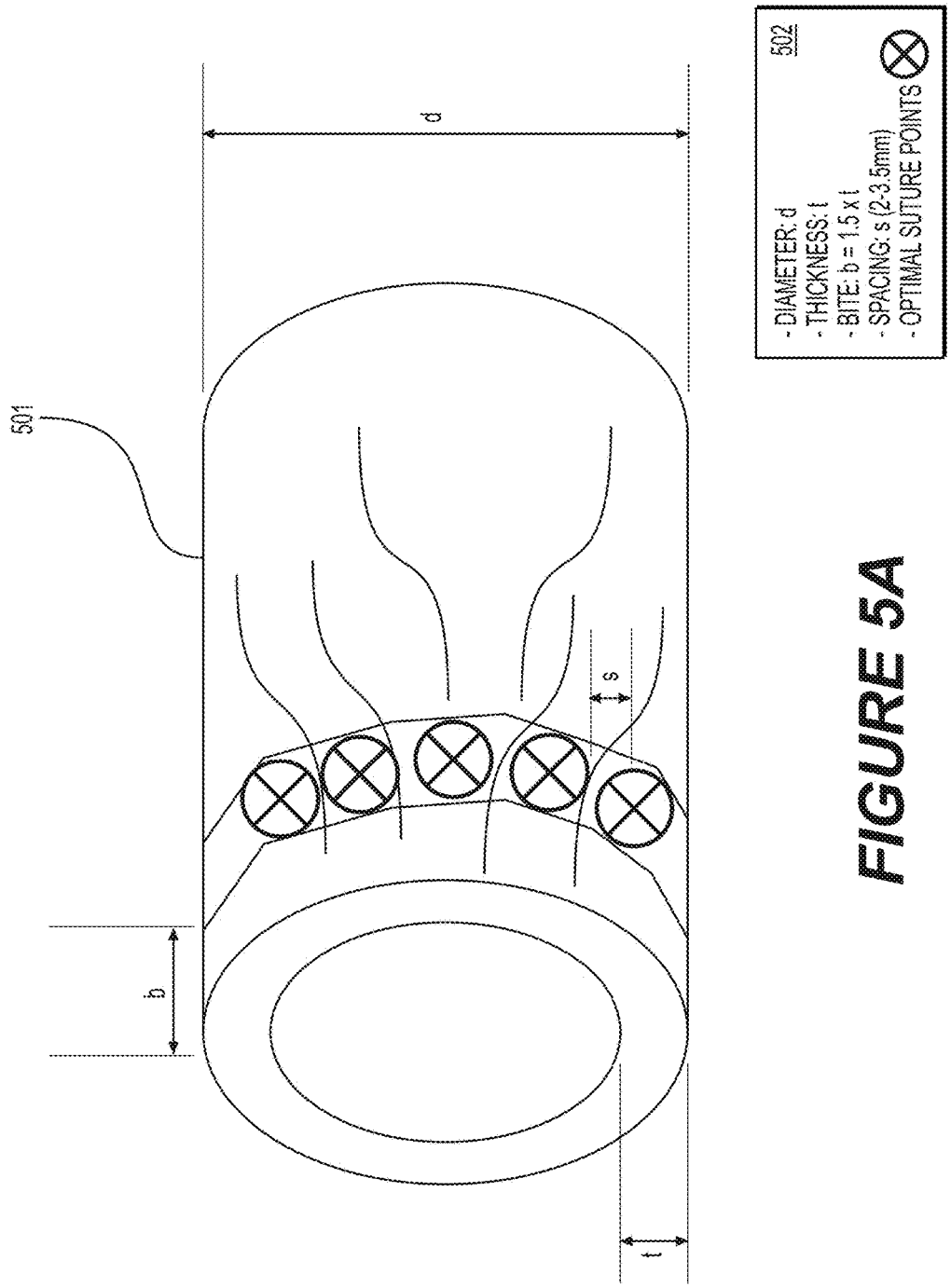
FIG. 5A illustrates determining specification of a bowel and optimal suture points.

FIG. 5A illustrates an embodiment for the specification of suture placement criteria for bowel anastomosis. Some of the criteria are implemented from numerical processing of the input multispectral images. For example thickness t of a bowel is calculated from the multispectral images. Some of the information is obtained from other sources. For example, bowel diameter d is obtained from age-specific atlas data. Bite distance from the edge of the bowel is provided by the expert surgeon and depends on the type of tissue.

In an exemplary embodiment, a tissue thickness map is determined from multispectral images. In many procedures, tissue thickness contributes to overall success of operation. An example is bowel anastomosis, where the thicker the tissue areas are, the higher the suture retention strength is. This means thicker tissue regions are more suitable suture placement candidates. Tissue thickness can be empirically found from multispectral images. The light reflected from the tissue surface retains the initial polarization but remaining part of the light penetrates deep into the tissue and loses their original polarization due to several scattering events. The penetration depth of optical radiation in the tissues depends on the wavelength of the light.

Diffuse reflectance (R) from the tissue provides morphological information from different depths, and using multispectral imaging it is possible to extract thickness information. The amount of diffuse reflectance (brightness) is measured at different wavelengths. Thicker tissue reflects more light than thinner tissue because light penetrates though thinner tissue easily and is not reflected. Distributions of structural and morphological parameters can be found based on the ratio between different spectral images as described in the equation below:

$$\frac{R(x, y, \lambda_k)}{R(x, y, \lambda_{reference})}$$

For example, a 470-nm cross-polarized spectral image is selected as a reference reflectance image. The reflectance ratios between different spectral images are calculated and compared for the thickness differentiation. In the above equation, x and y correspond to horizontal and vertical pixel coordinates, respectively, $\lambda_k$ corresponds to multispectral bandwidth for the k-th band, and $\lambda_{reference}$ corresponds to a reference bandwidth of, for example, a 470-nm cross-polarized spectral image.

A global reflectance R over the entire spectral range on tissue sample images can be described by the following equation:

$$R = \sum_{\lambda_k} R(x, y, \lambda_k)$$

Intra-tissue intrinsic spectral variability can be analyzed by removing the global reflectance (R), leading to the 'Spectral reflectance' $S(x, y, \lambda_k)$ on tissue based on the equation below:

$$S(\lambda_k) = R(\lambda_k) - R$$

Figure 5B:
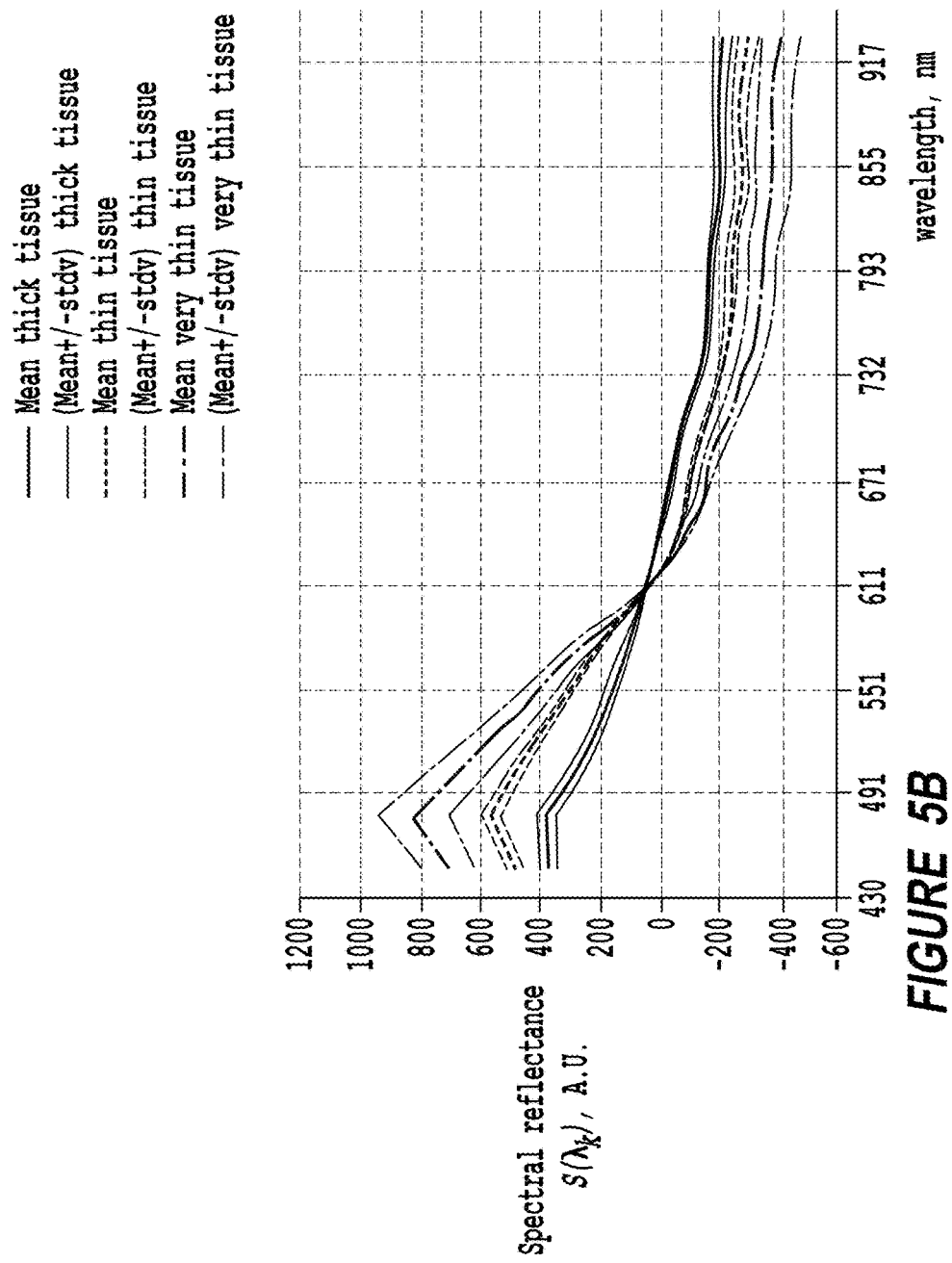
FIG. 5B illustrates an exemplary spectral reflectance chart.
Figure 6:
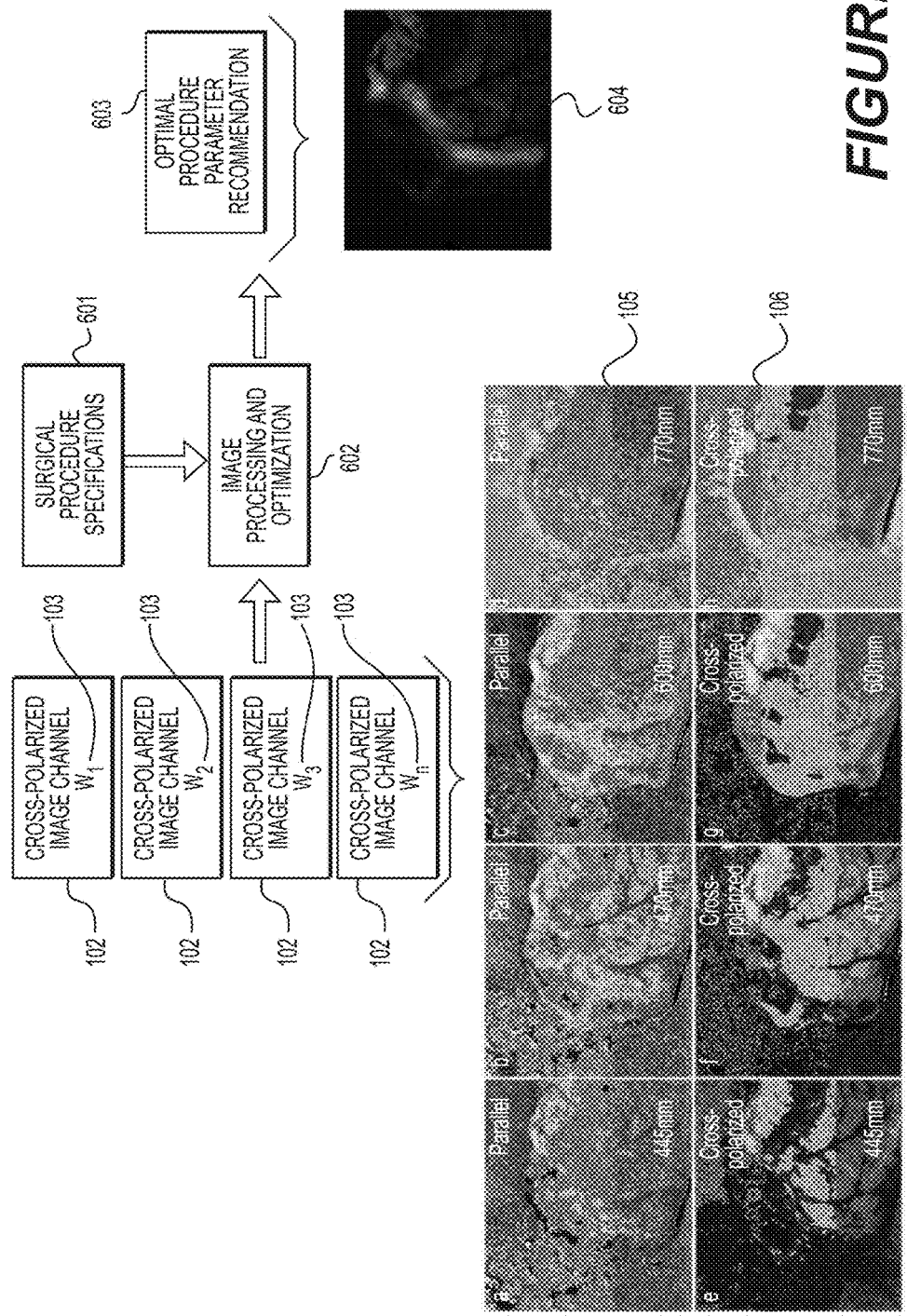
FIG. 6 illustrates an optimal parameter recommendation system corresponding to FIG. 2.

The spectral behavior of $S(\lambda_k)$ depends on the tissue thickness. For example, when the tissue becomes thicker, the Spectral reflectance decreases in the blue spectrum ranges and increases in the near infrared region, leading to the so-called "spectral rotation" around 600-nm as a function of tissue thickness (see chart below). Thus, the gradient (ratio) of Spectral reflectance between lower and upper wavelengths can be used to provide thickness information in tissue diffusive reflectance. See FIG. 5B.

FIG. 3 illustrates an optimal parameter recommendation system according to an exemplary embodiment. The system acquires multispectral images (for example, cross-polarized images 106 and/or parallel polarization images 105) at different wavelengths similar to what was described earlier with regard to FIG. 1. Based on surgical procedure specifications 601 which can be obtained from surgeons or learned from multiple repetitions of a surgical procedure or task using machine learning, numerical information and images are processed and optimal arguments of an optimization problem are found. For example, the image processing and optimization system 602 includes a processor and/or circuitry in order to process the multispectral images and to determine optimal arguments of the optimization problem.

The optimization problem describes the task of finding the optimal suture locations (or other points for surgery). The image processing and optimization system 602 processes, for example, the cross-polarized images 106 in order to determine a combined map, discussed earlier with regard to FIG. 2 (see also FIG. 11 for description of a combined map resulting from a fusion operator). The combined map described with regard to FIGS. 2 and 11 is used to determine, for example, optimal suture points. For example, the combined map may include an assigned value for each pixel based on how suitable it is for suturing. An optimization algorithm (executed using a particularly programmed processor and/or circuitry in the image processing and optimization system 602 and/or the optimal parameter recommendation system 603) finds a series of points with the highest values to create the optimum suture line. Parts feeding into the optimization algorithm are nominal suture spacing and bite sizes. Using the bite size, the optimization algorithm finds a suitable area around the nominal bite size away from the cutline (see image 704 in FIG. 7 and image 1003 in FIG. 10). In one embodiment, the optimization algorithm initializes at the highest value pixel in the image area, and then iteratively finds the best next suture point by selecting the highest value point that is at nominal suture spacing away from the previous point. Deviation from the nominal spacing and bite size feeds in negatively into the optimization algorithm.

Based on the optimization result of the optimization algorithm described above, the optimal procedure parameter recommendation system 603 recommends a set of acceptable procedure parameters which are optimal in the sense of the objective function used in defining the optimization problem in the image processing and optimization system 602. For example recommendations for optimal suture placements are generated and shown to the user by image overlay 604. Although image processing of multispectral images is generally described with regard to FIG. 6, image processing steps and optimal parameter recommendation for surgical procedure is further described with regard to FIG. 11.

Figure 7:
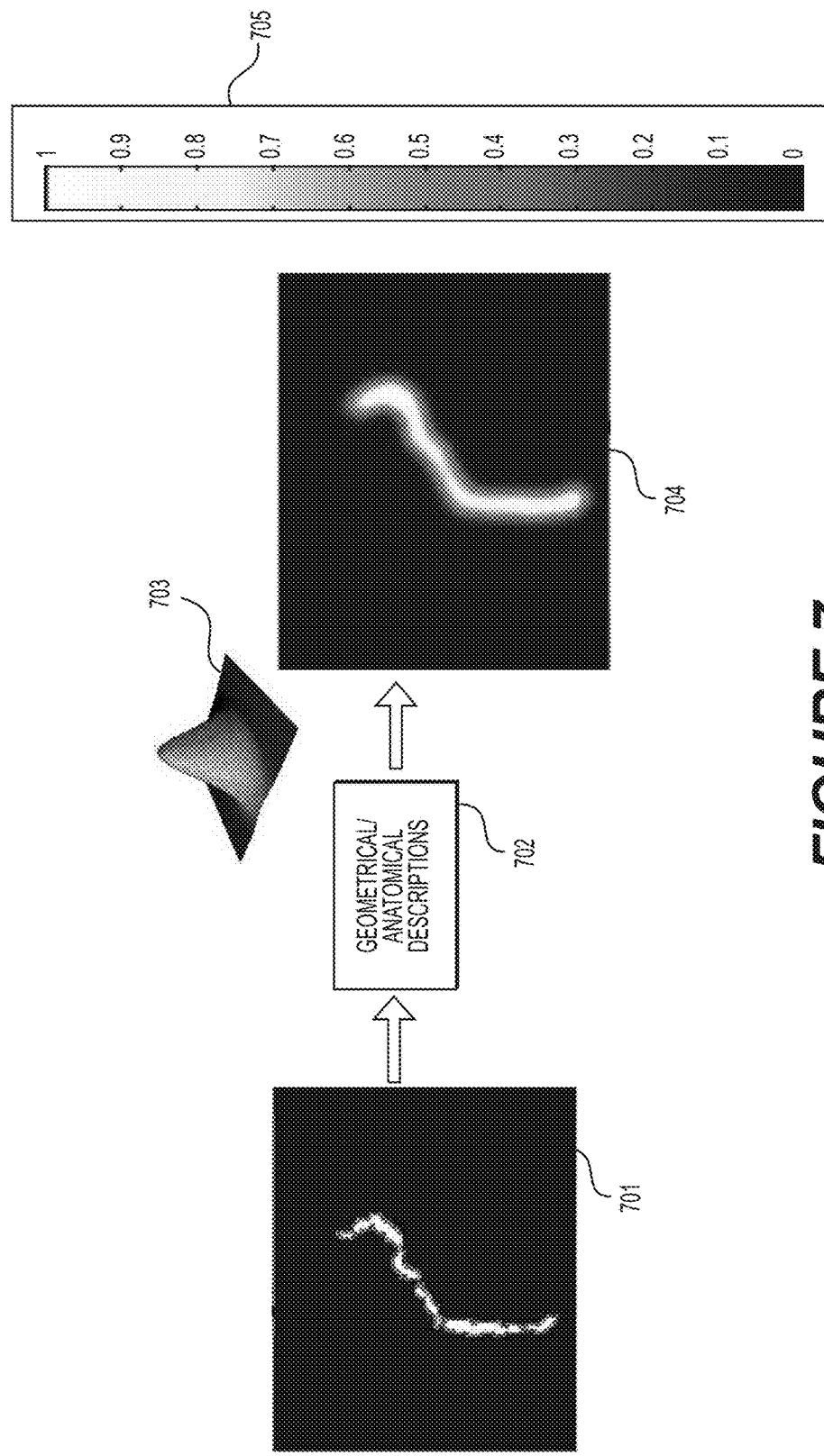
FIG. 7 illustrates the generation of a first gradient map from a first value map.

In an exemplary embodiment, as illustrated in FIG. 7, anatomical information and geometrical information are enumerated using smooth gradients. For example, approximately 2 cm on the left of an anatomical landmark (for example, the bowel cut line in image 701) is enumerated by a function that has a peak at 2 cm and gradually drops as it gets away from the peak. An example is a bell-shaped curve 703 which enumerates uncertain distances around the peak. For instance, an algorithm detects the cut line. Sutures are generally placed a nominal bite size away from the cut line, which creates a suture line. By convoluting this suture line with a bell curve, a gradient map 704 can be generated that describes the areas for good sutures geometrically (i.e. at the center of the line values are highest and appropriate for suture and going away from the line values are lower and not appropriate for suture).

Further, when there are two anatomical landmarks, a function is determined where a minimum of the function is determined to be on the landmarks and a peak of the function is determined to be approximately in between the landmarks. This allows for enumeration of approximate distance. The anatomical landmark shown in image 701 is the bowel cut line. Ideal suture locations are described as approximately 1.5 times the average tissue thickness provided in geometrical description 702 and encoded by a smooth filter implemented by the convolution operator 703. The result is a gradient map (or avoidance map) that illustrates an ideal distance from the cut line (see avoidance map 704) for a surgical procedure, where dark values correspond to 0 and bright values correspond to 1 as shown in a scale 705. As noted above, values closer to 1 refer to a less vulnerable region, whereas values closer to 0 refer to more vulnerable regions. The image 701 corresponds to image 207 in FIG. 2 and is processed by a processor and/or circuitry to form an gradient map 704 based on geometrical/anatomical descriptions 702 and a convolution operation 703 (for example, a smooth filer).

Figure 8:
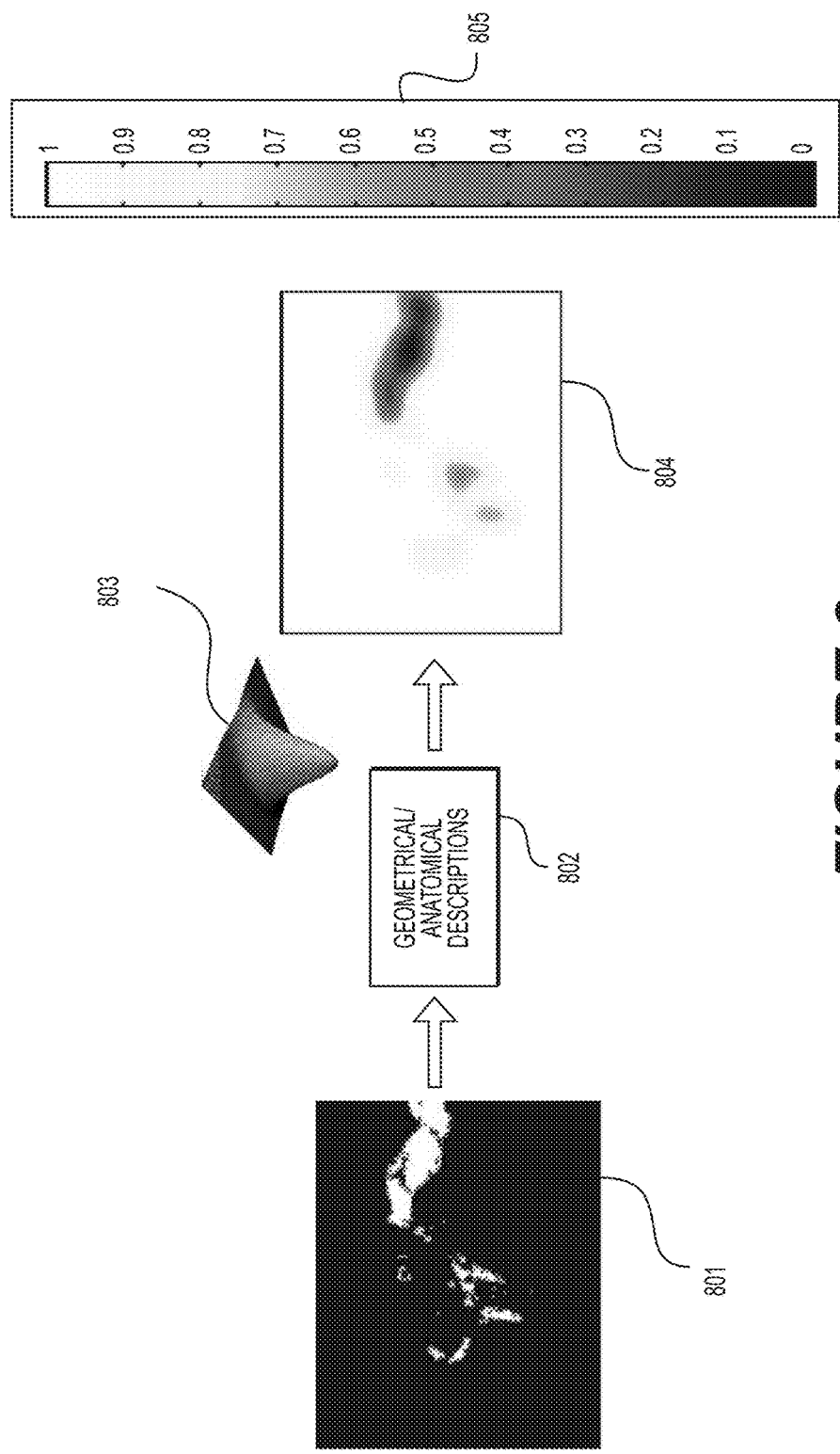
FIG. 8 illustrates the generation of a second gradient map from a second value map.

FIG. 8 illustrates an exemplary embodiment for encoding of anatomical information and generation of a corresponding gradient map 804. A value map 801, where white pixels are mesentery and black pixels are not mesentery, is processed by a processor and/or circuitry to form an gradient map 804 based on geometrical/anatomical descriptions 802 and a convolution operation 803 (for example, a smooth filer). In FIG. 8, the value map 801 corresponds to anatomical features corresponding to the mesenteric and other vulnerable tissue. The convolution of the value map 801 with an appropriate smooth filter 803 results in a gradient map 804 (or a normalized avoidance map), where dark values correspond to 0 and denote areas that must be avoided and bright values correspond to 1, as shown in a scale 805. The convolution, in this case, smoothens the value map 801 to generate the gradient map 804. As a result large mesentery regions can be avoided the strongest and very small mesentery areas or the very edges do not need to be avoided this strongly.

Figure 9:
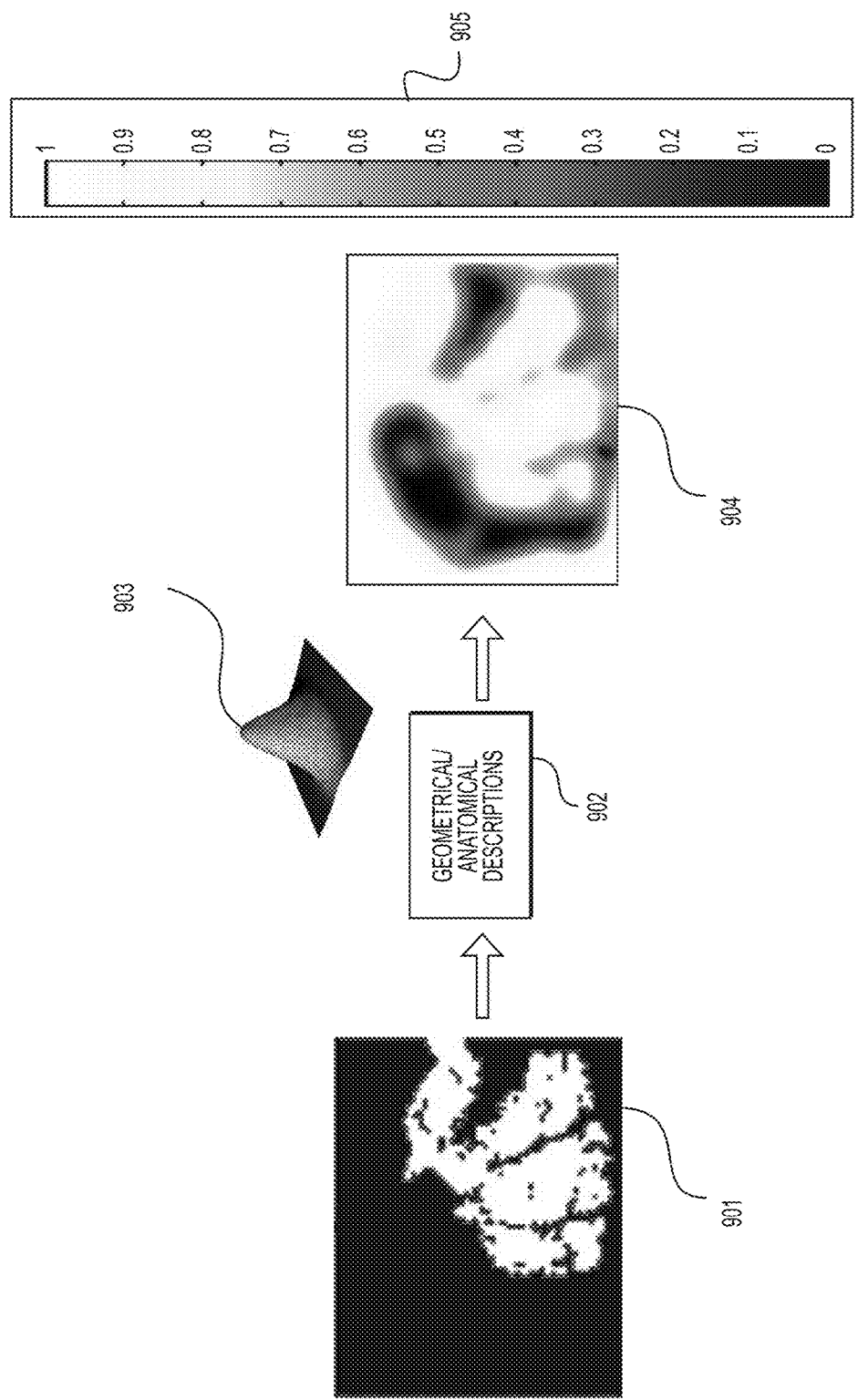
FIG. 9 illustrates the generation of a third gradient map from a third value map.

Similarly, FIG. 9 illustrates another embodiment for encoding of anatomical/geometrical description 902 and generation of a corresponding gradient map 904. The value map 901 is an output of the segmentation pipeline (i.e., corresponding to value map 205 in FIG. 2) and is described as a stable tissue (via the anatomical/geometrical description 902). The convolution of the value map 901 with an appropriate smooth filter 903 results in a gradient map 904 (or a normalized avoidance map), where dark values correspond to 0 (i.e., regions which should be avoided during a surgical procedure) and bright values correspond to 1 (i.e., regions that are appropriate for surgical procedure), as shown in a scale 905.

It should be noted that the images, maps, surgical procedure specifications, and geometrical/anatomical descriptions described throughout the specification can be stored in a single memory or multiple memories. Further, they can be acquired from a memory separate from the apparatus that performs image processing of the multispectral images or can be a part of the apparatus that performs image processing of the multispectral images. Also, the images, maps, surgical procedure specifications, and geometrical/anatomical descriptions can be displayed on a display.

Figure 10:
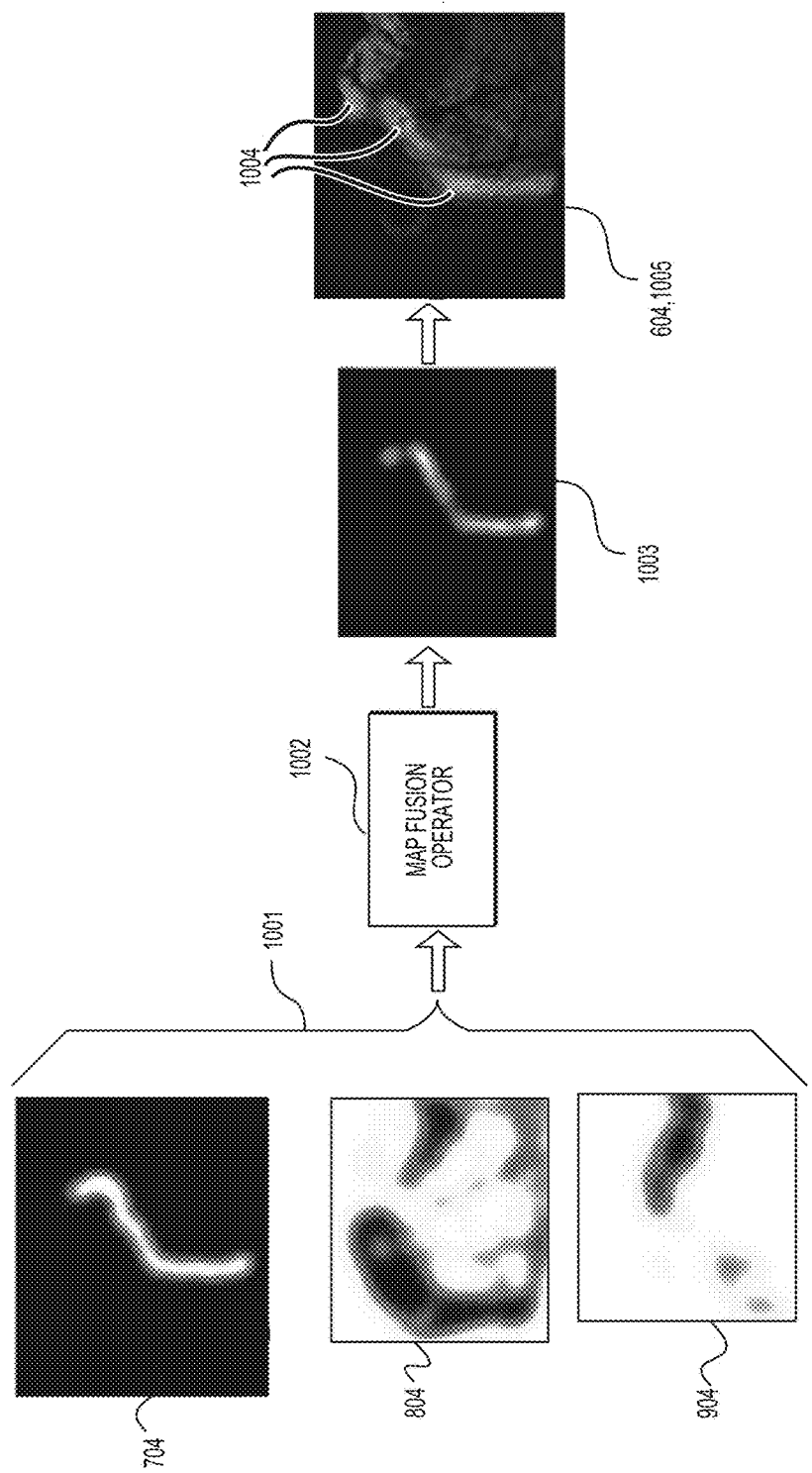
FIG. 10 illustrates a map fusion operator for generation of a recommendation map for determining optimal points for a medical surgical procedure.
Figure 11:
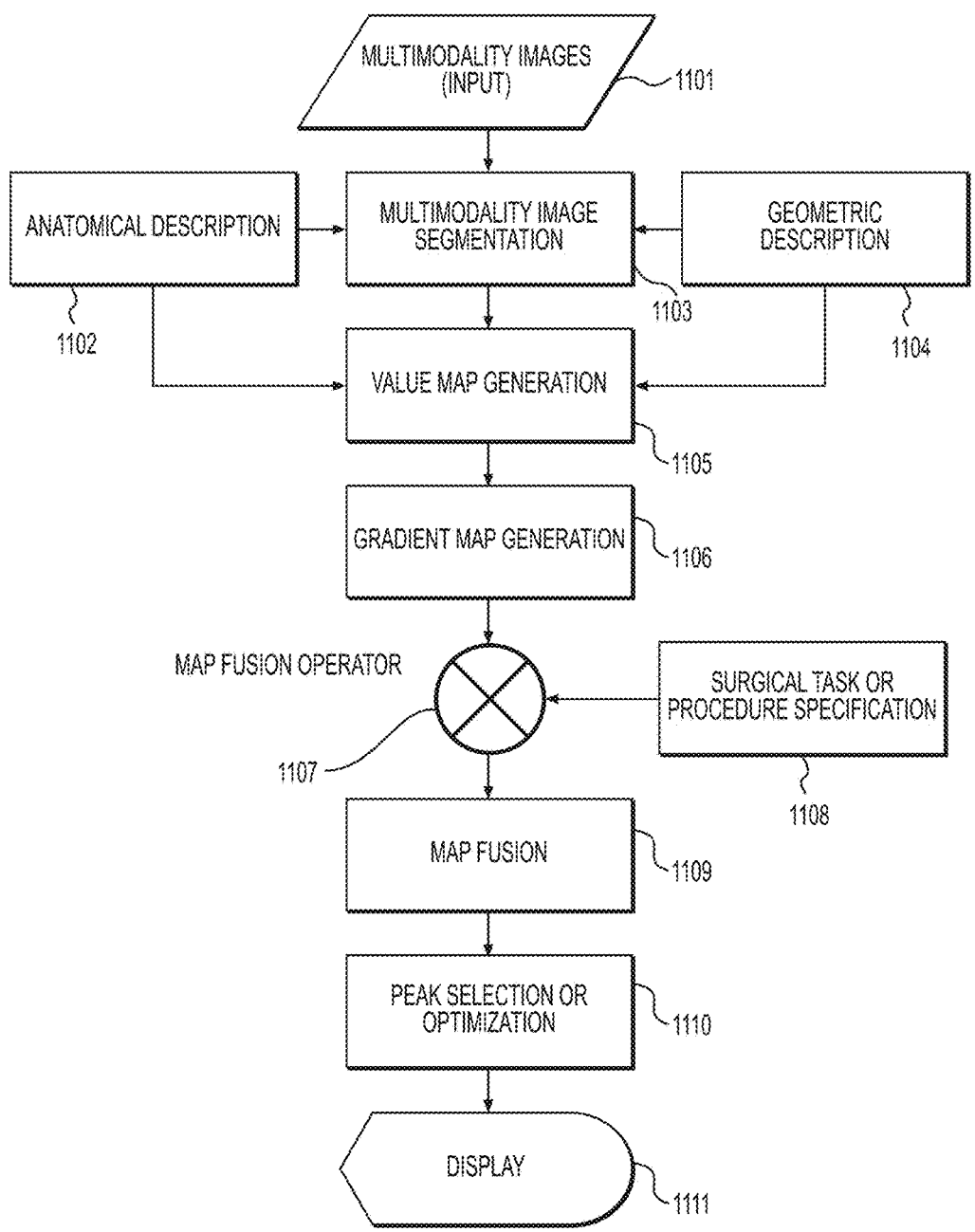
FIG. 11 illustrates a method for providing recommendation to a surgeon or a surgical system for a surgical procedure.

In an exemplary embodiment illustrated in FIG. 10, different gradient maps 1001 (corresponding to gradient maps 704, 804, and 904 in FIGS. 7, 8, and 9, respectively) derived from multispectral image processing and segmentation are fused by a mathematical fusion operator 1002 to obtain a recommendation map 1003 (for example, a suture map). An example of the operator that fuses these maps into a single recommendation map 1003 is the element-wise matrix multiplication operator. The map fusion operator 1002 includes a processor and/or circuitry to perform the operation of element-wise matrix multiplication. Although FIG. 10 illustrates fusing multiple gradient maps 1001, it should be understood that multiple value maps (see FIG. 2) can be fused together to form the recommendation map 1003. Additionally, the value maps described in FIG. 2 can be derived from multispectral images without segmenting the multispectral images. In other words, image processing can be performed on multispectral images to generate value maps (without the need for segmentation), which can be fused together to form a recommendation map 1003.

Based on the obtained recommendation map 1003, for example, optimal suture points 1004 can be calculated automatically with respect to a cost function defined over the map variables. The optimal point (or points or coordinates) p* can be defined as the solution the following optimization problem defined as:

$$p^* = \mathrm{argmax}_{b,t,m} J(b,t,m),$$

where function J is a cost function based on inputs such as the blood vessel map, thickness map, and multispectral segmentation maps. The method, addressing the above problem using a processor and/or circuitry, calculates the local maxima of the recommendation map 1003 and generates a set of recommendations for suture placements 1004 and shows them by image overlay on an original image 1005. The suture placements 1004 on an original image 1005 (of the patient's anatomy) are output from the system and are provided to the surgeon or the surgical system. This optimization problem is not convex and does not have a global maximum. Local maxima can be found and are shown to the surgeon as recommendations for suture placement.

The above method formalizes a mathematical optimization problem of finding the optimal coordinates, p*, by solving a numerical optimization problem. The objective function, J, is a mapping from parameters of the suturing map (b—for suture bite size parameter, t—for thickness parameter, and m—for smoothness parameter) to a normalized array the size of the image height times the image width, which has been previously defined as the suture map.

In its most basic form, the fusion operator 1002 and 1107 is the element-wise matrix multiplication between all segmented images and/or all value maps and/or all gradient maps from the previous steps. For example, if one of the maps describes the blood vessels, '0' corresponds to where there is a blood vessel which should be avoided. A piecewise multiplication ensures that any array elements with a "strong avoid" (that is '0') would definitely be avoided. If an array element has a value of 0.1 in the blood vessel map (that is very close to a blood vessel), but is thick region with a value of 0.75 in the thickness map, the piecewise multiplication for that pixel would be 0.075 (i.e., 0.1*0.75) which will be selected by the optimization. Relatively thick regions with, for example, a thickness score of 0.6, but away from blood vessels with a blood vessel score of 0.8, would result in a combined score of 0.6*0.8=0.48 which is much larger than a thicker tissue closer to a blood vessel (i.e., 0.075 noted above). These numerical examples are provided for better insight into the method for providing recommendation for optimal regions for a surgical procedure. A fusion operator can be defined as a multivariable function which takes numerical values in the range of 0 to 1 as inputs and outputs a numerical value in the range of 0 to 1. The present disclosure is not limited to the usage of element-wise matrix multiplication as the fusion operator. Other fusion operators can be used.

If J was a convex function, there would be one global maximum. The above-noted function J is nonconvex, which means that several local maxima can be found (i.e., several peaks can be found). An aspect of the present disclosure is to solve the optimization problem by finding the local peaks (one of them would be a global maximum). The coordinates of these peaks are output such that they provide recommendation for optimal regions for a surgical procedure.

Thick tissue regions can be programmed to have a larger spacing (3.5 mm), while thin areas can have a smaller spacing (2 mm) between sutures to compensate fragility with more suturing. This method is basically designed to avoid blood vessels and other vulnerable tissue areas for efficient suture placements. In an exemplary embodiment, nerves are imaged and the corresponding map is enumerated to avoid surgical procedures around the nervous system. In another exemplary embodiment, multi-modal imaging system uses Ultrasound, CT scans, X-ray images, MRI, functional MRI or other medical imaging techniques.

FIG. 11 illustrates a flowchart of a method for providing recommendation for a surgical procedure. In Step 1101 multi-modality images (i.e., multispectral images) are acquired from a multispectral imaging system (see FIG. 1). The multispectral images acquired may correspond to a single anatomy of a patient or various different anatomies of a patient. Anatomical information in Step 1102 and/or Geometric information in Step 1104 corresponding to a patient's anatomy are described and enumerated if required.

In Step 1103, the multispectral images are segmented using anatomical and/or geometric descriptions of the patient's anatomy to generate segmented images (see FIG. 2) that illustrate features or regions or sections of interest of a patient's anatomy. For example, the region of interest may include an inside layers of a porcine intestine, namely the mucosa, the mesentery, and some blood veins and arteries, an outer layer of the porcine intestine, namely the serosa, and/or a mesenteric layer and other vulnerable features around a cut line (see segmented images 201, 202, and 203 in FIG. 2). Further, Step 1105 also includes a step of performing image processing on the plurality of segmented images to generate a plurality of value maps corresponding to a different portion of the patient's anatomy (see value maps 205 and 206 in FIG. 2). Although FIG. 11 illustrates segmentation of the multispectral images prior to determining value maps, it should be noted that value maps can be generated from multispectral images without the segmentation step 1103. Further, the value maps can correspond to different maps (i.e., thickness map, blood vessel map, nerves map, or any other map that illustrates different portions/anatomical features of a patient's anatomy).

The value maps along with anatomical and geometric information are used to generate gradient maps in Step 1106. The gradient maps (also referred to as an avoidance map or a numerical map) are formed by the convolution of binary maps and an appropriate smooth filter (see FIGS. 7, 8, and 9). The gradient maps illustrate regions of a patient's anatomy that are appropriate for a surgical procedure and other portions of a patient's anatomy that are not appropriate for surgical procedure. For example, a gradient map includes dark values portions which denote areas of a patient's that must be avoided during a surgical procedure and bright portions which denote areas of a patient's anatomy that are suitable for a surgical procedure.

The gradient maps formed in Step 1106 are then fused into one single recommendation map in Step 1109 (see suturing map 1003 in FIG. 10) by a fusion operator in Step 1107. Although FIG. 11 illustrates that gradient maps are fused together, it should be noted that value maps and/or segmented images can also be fused together to form a single recommendation map. The surgical tasks or procedures obtained in Step 1108 dictates which maps are used by the operator and what type of mathematical operator should be used. An example of the fusion operator described in Step 1107 is a multiplication operator. As an example for suturing, tissue parameters relevant for suturing include perfusion, thickness, blood vessels, and tissue type, so all these maps can be multiplied. As an example for cutting, tissue type is important, so such a map can be used.

From the generated recommendation map in Step 1109, local peaks or maxima (for example, optimal suture points) can be determined in Step 1110 and displayed to the surgeon or the surgical system in Step 1111 (see FIG. 10). Local peaks and/or maxima can be determined by the above-noted equation described with regard to FIG. 10. An example of display to a surgeon includes displaying optimal suture points on an original image of a patient's anatomy (see FIGS. 6 and 10).

Figure 12:
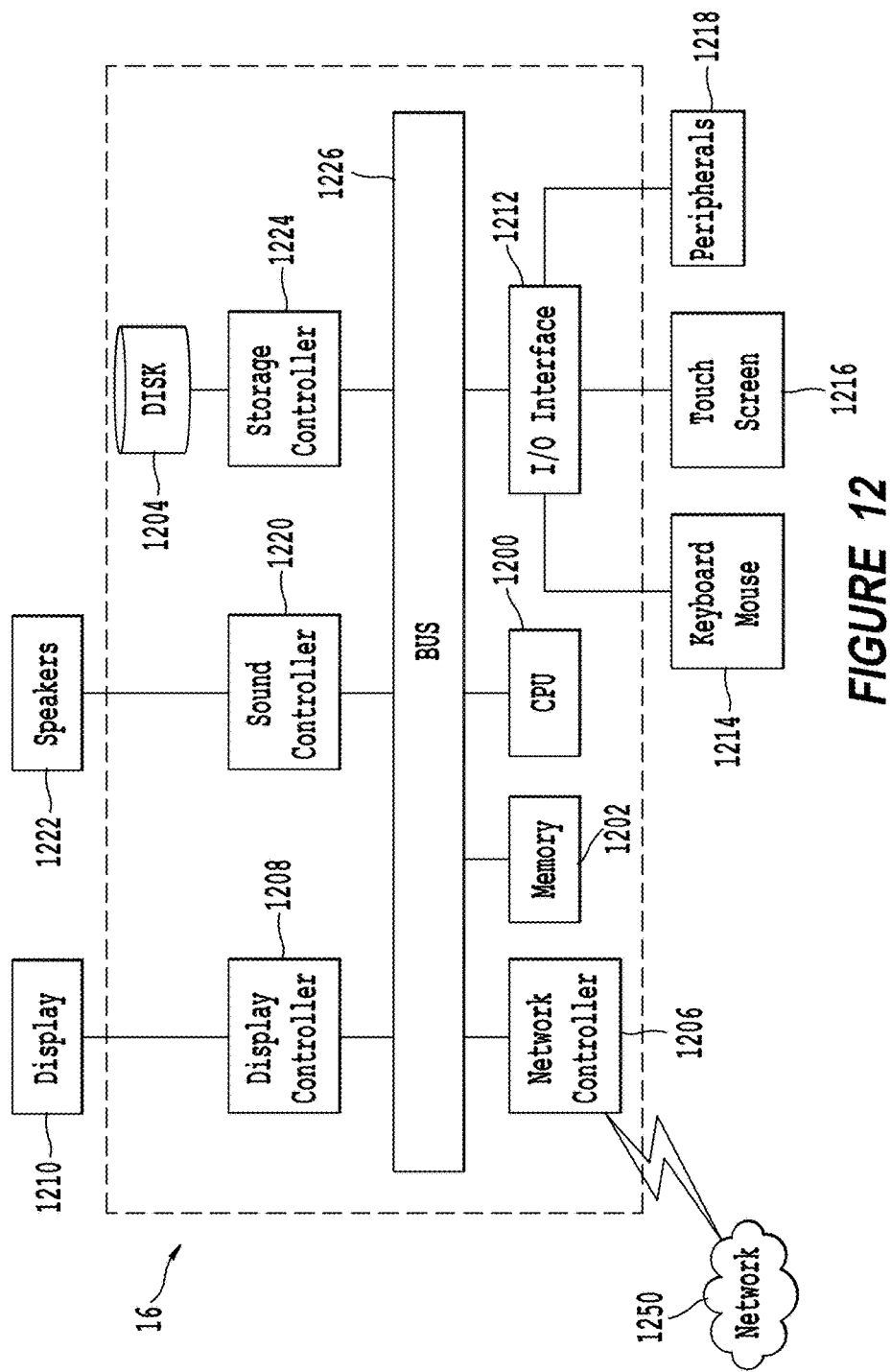
FIG. 12 illustrates an exemplary computing system.

Next, a hardware description of device 16 according to exemplary embodiments is described with reference to FIG. 12. In FIG. 12, the device 16 includes a CPU 1200 which performs the processes described above. The process data and instructions may be stored in memory 1202. These processes and instructions may also be stored on a storage medium disk 1204 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the device 16 communicates, such as a server or computer.

Further, the claimed advancements may be provided as a utility application, background daemon, or component of an operating system, or combination thereof, executing in conjunction with CPU 1200 and an operating system such as Microsoft Windows 7, UNIX, Solaris, LINUX, Apple MAC-OS, iOS, Android and other systems known to those skilled in the art.

CPU 1200 may be a processor from Intel of America, ARM processor, or processor from AMD of America, or may be other processor types that would be recognized by one of ordinary skill in the art. Alternatively, the CPU 1200 may be implemented on an FPGA, ASIC, PLD or using discrete logic circuits, as one of ordinary skill in the art would recognize. Further, CPU 1200 may be implemented as multiple processors cooperatively working in parallel to perform the instructions of the inventive processes described above.

The device 16 in FIG. 12 also includes a network controller 1206, such as an Intel Ethernet PRO network interface card from Intel Corporation of America, for interfacing with network 1250. As can be appreciated, the network 1250 can be a public network, such as the Internet, or a private network such as an LAN or WAN network, or any combination thereof and can also include PSTN or ISDN sub-networks. The network 1250 can also be wired, such as an Ethernet network, or can be wireless such as a cellular network including EDGE, 3G and 4G wireless cellular systems. The wireless network can also be WiFi, Bluetooth, or any other wireless form of communication that is known.

The device 16 further includes a display controller 1208, such as a graphics adaptor for interfacing with display 1210, such as a LCD monitor. A general purpose I/O interface 1212 interfaces with a keyboard and/or mouse 1214 as well as a touch screen panel 1216 on or separate from display 1210. General purpose I/O interface also connects to a variety of peripherals 1218 including printers and scanners.

A sound controller 1220 is also provided in the device 16 to interface with speakers/microphone 1222 thereby providing sounds and/or music.

The general purpose storage controller 1224 connects the storage medium disk 1204 with communication bus 1226, which may be an ISA, EISA, VESA, PCI, or similar, for interconnecting all of the components of the device 16. A description of the general features and functionality of the display 1210, keyboard and/or mouse 1214, as well as the display controller 1208, storage controller 1224, network controller 1206, sound controller 1220, and general purpose I/O interface 1212 is omitted herein for brevity as these features are known.

Obviously, numerous modifications and variations of the present disclosure are possible in light of the above teachings. It is therefore to be understood that within the scope of the appended claims, the embodiment may be practiced otherwise than as specifically described herein. For example, advantageous results may be achieved if the steps of the disclosed techniques were performed in a different sequence, if components in the disclosed systems were combined in a different manner, or if the components were replaced or supplemented by other components. The functions, processes, and algorithms described herein may be performed in hardware or software executed by hardware, including computer processors and/or programmable processing circuits configured to execute program code and/or computer instructions to execute the functions, processes, and algorithms described herein. A processing circuit includes a programmed processor, as a processor includes circuitry. A processing circuit also includes devices such as an application specific integrated circuit (ASIC) and conventional circuit components arranged to perform the recited functions.

The functions and features described herein may also be executed by various distributed components of a system. For example, one or more processors may execute these system functions, wherein the processors are distributed across multiple components communicating in a network. The distributed components may include one or more client and/or server machines, in addition to various human interface and/or communication devices (e.g., display monitors, smart phones, tablets, personal digital assistants (PDAs)). The network may be a private network, such as a LAN or WAN, or may be a public network, such as the Internet. Input to the system may be received via direct user input and/or received remotely either in real-time or as a batch process. Additionally, some implementations may be performed on modules or hardware not identical to those described. Accordingly, other implementations are within the scope that may be claimed.

It must be noted that, as used in the specification and the appended claims, the singular forms "a," "an," and "the" include plural referents unless the context clearly dictates otherwise.

While certain embodiments have been described, these embodiments have been presented by way of example only, and are not intended to limit the scope of the inventions. Indeed, the novel methods, apparatuses and systems described herein can be embodied in a variety of other forms; furthermore, various omissions, substitutions and changes in the form of the methods, apparatuses and systems described herein can be made without departing from the spirit of the inventions. The accompanying claims and their equivalents are intended to cover such forms or modifications as would fall within the scope and spirit of the inventions.

The invention claimed is:

1. A method for providing information for a medical surgical procedure, the method comprising:

acquiring, a processor, a plurality of multispectral images representing a portion of an anatomy of a patient;

performing image processing on each of the plurality of multispectral images to form a plurality of value maps, each value map identifying aspects of the portion of the anatomy of the patient by assigned values;

combining the plurality of value maps into a single recommendation map;

determining optimal points for performing the medical surgical procedure based on the single recommendation map;

displaying the optimal points for the medical surgical procedure by overlaying the optimal points on an original image of the portion of the anatomy of the patient or applying the optimal points to a robotic medical surgical procedure;

calculating diffuse reflectance values for the plurality of multispectral images;

selecting a reference diffuse reflectance value from the diffuse reflectance values and determining corresponding ratios between corresponding diffuse reflectance values and the reference diffuse reflectance value; and determining a thickness map, as one of the plurality of value maps, corresponding to thickness of different portions of the anatomy of the patient based on the determined corresponding ratios, wherein the optimal points for the medical surgical procedure are determined based on calculation of local maxima in the single recommendation map, which includes the thickness map, and wherein the medical surgical procedure is at least one of suturing and stapling and the optimal points is at least one of optimal suture and stapling points.

2. The method for providing information according to claim 1, further comprising:

extracting a foreground and a background from the plurality of multispectral images to extract blood vessels; and determining a vessel map, as one of the plurality of value maps, corresponding to vessels in different portions of the anatomy of the patient based on said extracting.

3. The method for providing information according to claim 1, further comprising:

analyzing proportions of corresponding signal intensity of the plurality of multispectral images; and determining a perfusion map, as one of the plurality of value maps, corresponding to an amount of blood perfusion in different portions of the anatomy of the patient based on said analyzing.

4. The method for providing information according to claim 2, wherein said extracting said foreground includes:

applying a blood vessel segmentation algorithm to the plurality of multispectral images; and extracting a centerline or a vessel skeleton from the plurality of multispectral images based on said blood vessel segmentation algorithm.

5. The method for providing information according to claim 2, wherein the optimal points for the medical surgical procedure are determined based on calculation of local maxima in the single recommendation map, which includes the vessel map.

6. The method for providing information according to claim 1, wherein the plurality of multispectral images are cross-polarized images.

7. The method for providing information according to claim 1, wherein the plurality of multispectral images are parallel polarization images.

8. The method for providing information according to claim 1, wherein the plurality of value maps include dark portions of the anatomy of the patient and bright portions of the anatomy of the patient, and wherein the dark portions of the anatomy of the patient indicate portions of the anatomy of the patient that need to be avoided during the medical surgical procedure and the bright portions of the anatomy of the patient indicate other portions of the anatomy of the patient that are appropriate for the medical surgical procedure.

9. The method for providing information according to claim 8, wherein the plurality of value maps include a scale indicating values from 0 to 1, wherein the values closer to 0 correspond to the dark portions of the anatomy of the patient and the values closer to 1 correspond to the bright portions of the anatomy of the patient.

10. The method for providing information according to claim 1, wherein each of the plurality of value maps corresponds to a different portion of the anatomy of the patient.

11. The method for providing information according to claim 1, wherein each of the plurality of value maps corresponds to a different anatomical feature of the anatomy of the patient.

12. The method for providing information according to claim 1, further comprising segmenting the representation of the portion of the anatomy of the patient to form a plurality of segmented images based on predetermined anatomical or geometric information.

13. An apparatus for providing information for a medical surgical procedure, the apparatus comprising:

a processor configured to:

acquire a plurality of multispectral images representing a portion of an anatomy of the patient;

perform image processing on each of the plurality of segmented images to form a plurality of value maps, each value map identifying aspects of the portion of the anatomy of the patient by assigned values;

combine the plurality of value maps into a single recommendation map;

determine optimal points for performing the medical surgical procedure based on the single recommendation map;

display the optimal points for the medical surgical procedure by overlaying the optimal points on an original image of the portion of the anatomy of the patient or apply the optimal points to a robotic medical surgical procedure;

calculate diffuse reflectance values for the plurality of multispectral images;

select a reference diffuse reflectance value from the diffuse reflectance values and determining corresponding ratios between corresponding diffuse reflectance values and the reference diffuse reflectance value; and determine a thickness map, as one of the plurality of value maps, corresponding to thickness of different portions of the anatomy of the patient based on the determined corresponding ratios, wherein the optimal points for the medical surgical procedure are determined based on calculation of local maxima in the single recommendation map, which includes the thickness map, and wherein the medical surgical procedure is at least one of suturing and stapling and the optimal points is at least one of optimal suture and stapling points.

14. The apparatus for providing information according to claim 13, wherein the processor is configured to:

extract a foreground and a background from the plurality of multispectral images to extract blood vessels, and determine a vessel map, as one of the plurality of value maps, corresponding to vessels in different portions of the anatomy of the patient based on the extracted foreground and background.

15. The apparatus for providing information according to claim 13, wherein the processor is configured to:

analyze proportions of corresponding signal intensity of the plurality of multispectral images; and determine a perfusion map, as one of the plurality of value maps, corresponding to an amount of blood perfusion in different portions of the anatomy of the patient based on said analyzed proportions.

16. The apparatus for providing information according to claim 14, wherein the processor is configured to:

apply a blood vessel segmentation algorithm to the plurality of multispectral images, and extract a centerline or a vessel skeleton from the plurality of multispectral images based on said blood vessel segmentation algorithm in order to extract the foreground.

17. The apparatus for providing information according to claim 14, wherein the optimal points for the medical surgical procedure are determined based on calculation of local maxima in the single recommendation map, which includes the vessel map.

18. The apparatus for providing information according to claim 13, wherein the plurality of multispectral images are at least one of cross-polarized images and parallel polarization images.

19. The apparatus for providing information according to claim 13, wherein the plurality of value maps include dark portions of the anatomy of the patient and bright portions of the anatomy of the patient, and wherein the dark portions of the anatomy of the patient indicate portions of the anatomy of the patient that need to be avoided during the medical surgical procedure and the bright portions of the anatomy of the patient indicate other portions of the anatomy of the patient that are appropriate for the medical surgical procedure.

20. The apparatus for providing information according to claim 15, wherein the plurality of value maps include a scale indicating values from 0 to 1, wherein the values closer to 0 correspond to the dark portions of the anatomy of the patient and the values closer to 1 correspond to the bright portions of the anatomy of the patient.

21. A non-transitory computer-readable storage medium including computer-readable instructions, that when executed by a computer, cause the computer to execute a method for providing information for a medical surgical procedure, the method comprising:

acquiring a plurality of multispectral images representing a portion of an anatomy of the patient;

performing image processing on each of the plurality of multispectral images to form a plurality of value maps, each value map identifying aspects of the portion of the anatomy of the patient by assigned values;

combining the plurality of value maps into a single recommendation map;

determining optimal points for performing the medical surgical procedure based on the single recommendation map;

displaying the optimal points for the medical surgical procedure by overlaying the optimal points on an original image of the portion of the anatomy of the patient or applying the optimal points to a robotic medical surgical procedure;

calculating diffuse reflectance values for the plurality of multispectral images;

selecting a reference diffuse reflectance value from the diffuse reflectance values and determining corresponding ratios between corresponding diffuse reflectance values and the reference diffuse reflectance value; and determining a thickness map, as one of the plurality of value maps, corresponding to thickness of different portions of the anatomy of the patient based on the determined corresponding ratios, wherein the optimal points for the medical surgical procedure are determined based on calculation of local maxima in the single recommendation map, which includes the thickness map, and wherein the medical surgical procedure is at least one of suturing and stapling and the optimal points is at least one of optimal suture and stapling points.

* * * * *